US009195799B2

United States Patent
Sze et al.

(10) Patent No.: US 9,195,799 B2
(45) Date of Patent: Nov. 24, 2015

(54) WIRELESS PATIENT MONITORING SYSTEM

(75) Inventors: Cheng-Feng Sze, San Jose, CA (US); Augustine Lien, Palo Alto, CA (US)

(73) Assignee: AULISA MEDTECH INTERNATIONAL, INC., Taipei (TW)

( * ) Notice: Subject to any disclaimer, the term of this patent is extended or adjusted under 35 U.S.C. 154(b) by 944 days.

(21) Appl. No.: 13/369,264

(22) Filed: Feb. 8, 2012

(65) Prior Publication Data

US 2012/0203078 A1 Aug. 9, 2012

Related U.S. Application Data

(60) Provisional application No. 61/440,721, filed on Feb. 8, 2011.

(51) Int. Cl.
*A61B 5/00* (2006.01)
*G06F 19/00* (2011.01)

(52) U.S. Cl.
CPC .............. *G06F 19/3418* (2013.01); *A61B 5/746* (2013.01); *A61B 5/747* (2013.01); *G06F 19/322* (2013.01); *G06F 19/327* (2013.01); *G06F 19/3406* (2013.01)

(58) Field of Classification Search
USPC .................................. 600/300–301, 323–324
See application file for complete search history.

(56) References Cited

U.S. PATENT DOCUMENTS

| | | | | |
|---|---|---|---|---|
| 7,860,583 B2 * | 12/2010 | Condurso et al. | .................. | 700/2 |
| 8,328,420 B2 * | 12/2012 | Abreu | ........................... | 374/208 |
| 8,965,473 B2 * | 2/2015 | Hoarau et al. | ................. | 600/323 |
| 2003/0028085 A1 * | 2/2003 | Al-Ali | ............................ | 600/323 |
| 2004/0122297 A1 * | 6/2004 | Stahmann et al. | ............. | 600/300 |
| 2005/0245831 A1 * | 11/2005 | Banet | ............................ | 600/485 |
| 2006/0200009 A1 * | 9/2006 | Wekell et al. | ................. | 600/300 |
| 2007/0249944 A1 * | 10/2007 | Fischell et al. | ................ | 600/509 |
| 2007/0258395 A1 * | 11/2007 | Jollota et al. | .................. | 370/310 |
| 2008/0256048 A1 * | 10/2008 | Hayter | .............................. | 707/4 |
| 2009/0030285 A1 * | 1/2009 | Andersen | ....................... | 600/300 |
| 2009/0054743 A1 * | 2/2009 | Stewart | .......................... | 600/301 |
| 2009/0216141 A1 * | 8/2009 | Fischell | ............... | A61B 5/0031 600/509 |
| 2010/0056886 A1 * | 3/2010 | Hurtubise et al. | ............. | 600/324 |
| 2010/0312188 A1 * | 12/2010 | Robertson et al. | ............. | 604/156 |
| 2010/0331638 A1 * | 12/2010 | Besko | ............................ | 600/323 |
| 2011/0001605 A1 * | 1/2011 | Kiani et al. | ..................... | 340/5.6 |
| 2011/0105854 A1 * | 5/2011 | Kiani et al. | ..................... | 600/300 |
| 2011/0224518 A1 * | 9/2011 | Tindi et al. | ...................... | 600/323 |
| 2012/0108911 A1 * | 5/2012 | Drysdale | ............. | G06F 19/3418 600/300 |
| 2012/0143012 A1 * | 6/2012 | Watson et al. | ................. | 600/300 |
| 2014/0142403 A1 * | 5/2014 | Brumback et al. | ............. | 600/324 |
| 2014/0243626 A1 * | 8/2014 | Krishnan et al. | ............... | 600/323 |
| 2014/0243628 A1 * | 8/2014 | Ochs et al. | ...................... | 600/324 |
| 2014/0276167 A1 * | 9/2014 | Dasgupta et al. | .............. | 600/529 |

(Continued)

*Primary Examiner* — William Thomson
*Assistant Examiner* — Bobby Soriano
(74) *Attorney, Agent, or Firm* — Venture Pacific Law, PC

(57) ABSTRACT

A patient monitoring system for monitoring vital signs, comprises: one or more sensors, wherein the sensors measure vital signs; a monitor station; and one or more portable monitoring devices, wherein monitored data based on the measured vital signs is wirelessly transmitted from the sensors to the monitor station, wherein the monitor station issues one or more alarms to certain ones of the portable monitoring devices as a function of the monitored data, and wherein a portion of the monitored data that pertains to the alarms is wirelessly transmitted to the certain ones of the portable monitoring devices and displayed by the certain ones of the portable monitoring devices.

16 Claims, 21 Drawing Sheets

(56) References Cited

U.S. PATENT DOCUMENTS

| | | |
|---|---|---|
| 2014/0296658 A1* | 10/2014 | Yuen et al. ............ 600/301 |
| 2014/0371547 A1* | 12/2014 | Gartenberg et al. .......... 600/301 |
| 2014/0378787 A1* | 12/2014 | Brumback et al. ............ 600/301 |

* cited by examiner

| Sensor ID | Sensor Class | Passcode | Encryption Key | Reserved | CRC |

Fig. 11

| Sensor ID | Sensor Class | Package Number | Data Type | Data Length | Data0 | Data1 | ...... | DataN | CRC |

Fig. 12

| Monitor ID | Time Stamp | Patient ID | Sensor ID | Sensor Class | Package Number | Data Type | Data Length | Data0 | Data1 | ...... | DataN | CRC |

Fig. 13

WIRELESS PATIENT MONITORING SYSTEM

CROSS REFERENCE

This application claims priority from a provisional patent application entitled "METHOD AND APPARATUS FOR WIRELESSLY MONITORING A SINGLE PATIENT OR A GROUP OF PATIENTS" filed on Feb. 8, 2011 and having an Application No. 61/440,721. Said application is incorporated herein by reference.

FIELD OF INVENTION

This invention generally relates to systems, apparatuses, and methods for patient monitoring and, in particular, to systems, apparatuses, and methods for wirelessly monitoring vital signs of patients.

BACKGROUND

Monitoring a patient's vital signs is very important during hospitalization, especially for a surgical operation, recovery, intensive care, and other medical reasons. Patient monitoring systems have become commonplace and are standard in hospitals. Typically, patient monitoring systems have sensors for monitoring vital signs that are connected to a patient via various wires, e.g., between a monitor station and the sensors. Thus, it is necessary to place the monitor station in close proximity to the patient due to the limitation of the length of the connecting wires.

A patient care provider, including a parent, midwife, nurse, doctor, home care provider, or other health care practitioner, is usually required to go to the patient's bedside to periodically check the vital signs of the patient. In addition, the patient care provider also determines whether any alarm or abnormal condition is triggered by manually checking the vital signs of the patient or by viewing the vital signs on a bedside monitor. The frequency that the patient care provider checks the patient's vital signs decides the response time to an emergency condition for the patient. Therefore, it is desirable to provide a monitoring station that displays the patient's condition and issues an alarm for the patient, to reduce the response time by the nurse or other patient care provider when the patient is in an emergency condition. Furthermore, it is also desirable to provide systems, methods, and apparatuses for a portable monitoring device to keep the nurse apprised of the patient's status and receive any alarms regarding any emergency condition for the patient.

When the patient moves from one place to another place, e.g., from the operating room to the recovery room, the wires for the vital sign sensors are disconnected from the bedside monitor in the operating room and then reconnected to the bedside monitor in the recovery room upon the patient's arrival. During the relocation of the patient, vital signs are not monitored unless there is a bedside monitor that travels with the patient. Not monitoring the patient can be very dangerous. For instance, if a critical condition happens during the relocation of the patient, then the health care provider is not given any indication of such critical condition. If there is a bedside monitor accompanying the patient, the bedside monitor is connected to the patient via connecting wires, which can be very inconvenient since the connected wires to the patient reduce the patient's mobility. Therefore, it is desirable to have a patient monitoring system that can continuously monitor the patient's vital signs without interruption, even during the relocation of the patient, and can easily determine the patient's vital sign data without having to disconnect and reconnect the sensor's wires to the patient.

Patient monitoring systems are also widely used at home or in a home care environment. For instance, monitoring an infant at home is an application of in-home monitoring. Sudden infant death syndrome ("SIDS") was responsible for 0.543 deaths per 1,000 live births in the United States ("US") in 2005. Although the cause of the deaths is still unknown, many prevention steps, including altering an infant's sleep positions and bedding, were suggested and have effectively reduced the fatality rate of infants. However, in many other cases, such as improper sleeping positions (e.g., sleeping face down) or using dangerous bedding, the infant can suffocate to death. Therefore, it is desirable to provide a wireless monitoring system that continuously monitors the blood oxygen saturation ("SpO2") of the infant during sleep to provide the infant's parents (or other infant care provider) an early alert to prevent the blood oxygen of the infant from reaching a fatal level. In addition, it is desirable to provide wireless systems, apparatuses, and methods for having live video images of the infant's activities and sleeping positions.

SUMMARY OF INVENTION

An object of this invention is to provide systems, apparatuses, and methods for wirelessly monitoring vital signs of patients.

Another object of this invention is to provide systems, apparatuses, and methods for a wireless portable monitoring device that remotely monitors a patient's vital signs and generates alarms for various medical emergencies.

Yet another object of this invention is to provide systems, apparatuses, and methods for a battery powered pulse oximeter.

Briefly, the present invention discloses a patient monitoring system for monitoring vital signs, comprising: one or more sensors, wherein the sensors measure vital signs; a monitor station; and one or more portable monitoring devices, wherein monitored data based on the measured vital signs is wirelessly transmitted from the sensors to the monitor station, wherein the monitor station issues one or more alarms to certain ones of the portable monitoring devices as a function of the monitored data, and wherein a portion of the monitored data that pertains to the alarms is wirelessly transmitted to the certain ones of the portable monitoring devices and displayed by the certain ones of the portable monitoring devices.

An advantage of this invention is that systems, apparatuses, and methods for wirelessly monitoring vital signs of patients are provided.

Another advantage of this invention is that systems, apparatuses, and methods for a wireless portable monitoring device that remotely monitors a patient's vital signs and generates alarms for various medical emergencies are provided.

Yet another advantage of this invention is that systems, apparatuses, and methods for a battery powered pulse oximeter are provided.

DESCRIPTION OF THE DRAWINGS

The foregoing and other objects, aspects, and advantages of the invention can be better understood from the following detailed description of the preferred embodiment of the invention when taken in conjunction with the accompanying drawings in which:

FIG. 11 illustrates a data format for a data package that is transmitted to a patient monitor and contains sensor set up information.

FIG. 12 illustrates a data format for a data package that is transmitted from a sensor to its paired bedside monitor.

FIG. 13 illustrates a data format for a data package transmitted from a bedside monitor to a monitor station.

DETAILED DESCRIPTION OF THE PREFERRED EMBODIMENTS

In the following detailed description of the embodiments, reference is made to the accompanying drawings, which form a part hereof, and in which is shown by way of illustration of specific embodiments in which the present invention may be practiced.

Generally, the present invention relates to monitoring vital signs and other conditions of a patient (or a group of patients), including environmental conditions for the patient, video images of the patient, audio recordings of the patient, and the physical location of the patient. The monitored data, which includes the patient's vital signs, video images, audio recordings, environmental conditions, location, and/or other patient data, is wirelessly transmitted from sensors on the patient to a remote monitor station via a bedside monitor or other communications device. When the monitored data falls outside certain preset parameters, an alarm is issued to alert the patient care provider. A portable monitoring device, wearable by the patient care provider, is designed to wirelessly receive the alarm and the monitored data.

The monitored data can be wirelessly transmitted from the sensors on the patient to any nearby bedside monitor. Thus, a patient's vital signs can be displayed on any bedside monitor without having to disconnect and reconnect wires from the patient's sensors to a wired monitor. The monitored data can also be recorded and stored for future reference or review. It is important to note that a bedside monitor can travel with the patient, whether or not the patient is in a bed. For instance, the bedside monitor may accompany a patient wherever the patient travels and in whatever mode of transportation the patient takes, including a movable bed, a wheelchair, an automobile, a plane, a helicopter, a bicycle, a motor boat, a crib, a cart, the patient's own power, some else's power, or any other form of travel.

Figure 1:
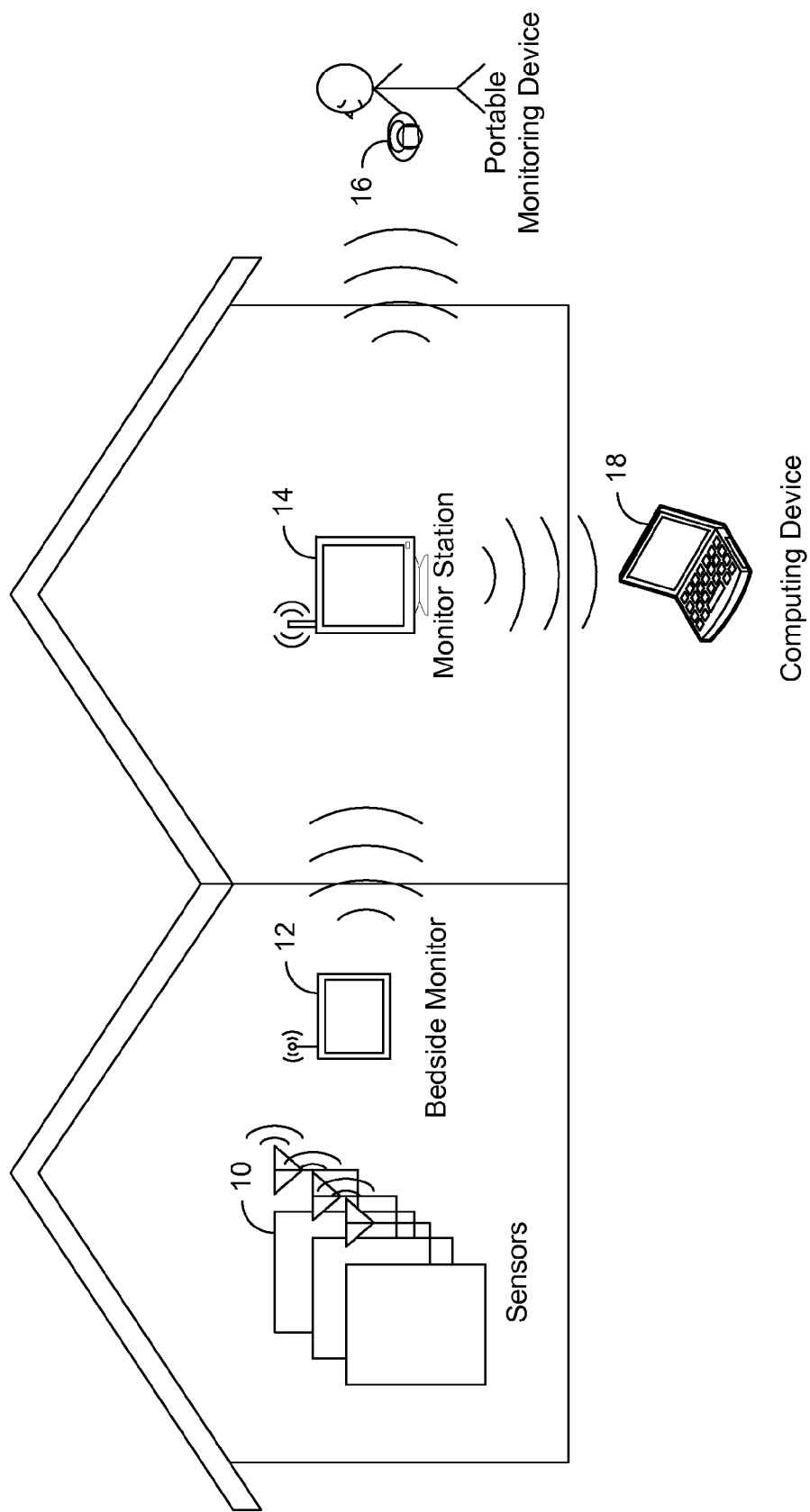
FIG. 1 illustrates a diagram of a patient monitoring system of the present invention for monitoring a patient.

FIG. 1 illustrates a diagram of a patient monitoring system of the present invention for monitoring a patient. The patient monitoring system can comprise sensors 10, a bedside monitor 12, a monitor station 14, a portable monitoring device 16 that can be worn or carried by a patient care provider, and a computing device 18 having application software, data storage, and a wireless transceiver. The bedside monitor 12 may also have a video camera and microphone to record and wirelessly transmit video and/or audio recordings of the patient to the monitor station 14. The bedside monitor 12 also can receive the monitored data through wireless transmissions from the sensors 10 and transmit the monitored data to the monitor station 14. In some embodiments of the present invention, the bedside monitor 12 can comprise a display screen for displaying part or all of the monitored data.

The sensors 10 can continuously measure the patient's vital signs such as the patient's oxygen saturation, pulse rate, body temperature, blood pressure, and/or other patient conditions. When the vital sign measurements (or other monitored data) are available, the sensors 10 wirelessly transmit that monitored data to the bedside monitor 12. The sensors 10 are designed to be low powered and transmit short range wireless transmissions to the bedside monitor 12. Therefore, the bedside monitor 12 may need to be located within a predefined range of the sensors 10 to be able to receive wireless transmission from the sensors 10. The bedside monitor 12 can have a built-in video camera with microphone to monitor the patient's activity and can include environmental sensors to monitor many of the environmental conditions such as the room temperature, humidity, etc.

The bedside monitor 12 can be plugged into a power outlet for a continuous power supply or be powered by a battery. Typically, power is not a constraint for the bedside monitor 12, which can transmit the monitored data wirelessly, at a relatively long range, to the monitor station 14. In this way, the bedside monitor 12 serves as a communications device by repeating the monitored data to the monitor station 14. By using the bedside monitor 12 to repeat the monitored data from the sensors 10, long range patient monitoring becomes possible since the monitor station 14 can relay the monitored data to the portable monitoring device 16. The bedside monitor 12 can undergo the following steps: receive the vital sign data from the sensors 10; then pack the vital sign data with the audio and video data and environment data; and finally wirelessly transmit this monitored data to the monitor station 14. The bedside monitor 12 can also include a warning light that can be controlled by the monitor station 14. In monitoring a group of patients, bedside monitors can each have a built-in display screen to display the respective patient's monitored data that is assigned to each of the bedside monitors.

The monitor station 14 is the main data processing center for receiving the monitored data from the bedside monitor 12 (and other bedside monitors), and processing the monitored data. The monitor station 14 can also display the monitored data on a display screen at the monitor station 14 and play the audio/video data of the patient. The monitor station 14 may also store the monitored data for future use either in local storage or in a computing device 18.

When scheduled, the monitor station 14 broadcasts part or all of the monitored data to the portable monitoring device 16 and/or the computing device 18. The programming software of the monitor station 14 can have various preloaded alert conditions to determine whether the monitored data has met one or more of the alert conditions. The alert conditions are programmable and can be set upon the direction of the patient's medical physician or other patient care provider. When an alert condition is triggered, the monitor station 14 will display the warning message on the display screen at the monitor station 14 and issue a warning sound and signal, e.g., via a flashing light-emitting diode ("LED") at the monitor station 14. The monitor station 14 can also transmit an alert to the bedside monitor 12 to initiate a warning signal at the bedside monitor 12, e.g., via a flashing LED on the bedside monitor 12. Also, the alert can also be transmitted to the portable monitoring device 16 to alert the patient care provider for that patient.

Since the patient care provider can wear or otherwise carry the portable monitoring device 16, the patient care provider does not have to be physically located at the monitor station 14. This allows patient care provider freedom to attend his/her other duties that are physically located elsewhere from the monitor station 14, while still being able to closely monitor the patient. Thus, the patient care provider can be alerted to and check on the patient's conditions at any time using the portable monitoring device 16. For instance, when there is an alert issued by the monitor station 14 or the bedside monitor 12, the portable monitoring device 16 can alert the patient care provider by either an audio alarm, a visual alarm, tactile alarm (e.g., a vibration), or a combination of the aforementioned alarm types. The portable monitoring device 16 can also have a small display screen (e.g., a liquid crystal display, "LCD") for displaying the warning condition.

When monitoring the patient, the monitor station 14 has a limited data storage capacity to store the monitored data. Generally, the monitor station 14 can store the most current monitored data for a predefined amount of time (e.g., 48 hours) for possible recall of that current monitored data. To store the monitored data going back for a longer period of time, the monitored data can be transmitted via a wireless or wired connection to the computing device 18 for storage.

In alternative embodiments of the present invention, the computing device 18 stores the monitored data on an external storage device, e.g., a USB flash memory stick or other external storage device. Once the computing device 18 stores the monitored data from the monitor station 14 on its storage device, such as a hard drive, computer software can analyze and graphically represent the monitored data. The analyzed data and graphical representations of the monitored data can then be copied to the external storage device to be delivered to the patient's medical physician for diagnosis or transmitted via a network connection to the patient's medical physician.

Figure 2:
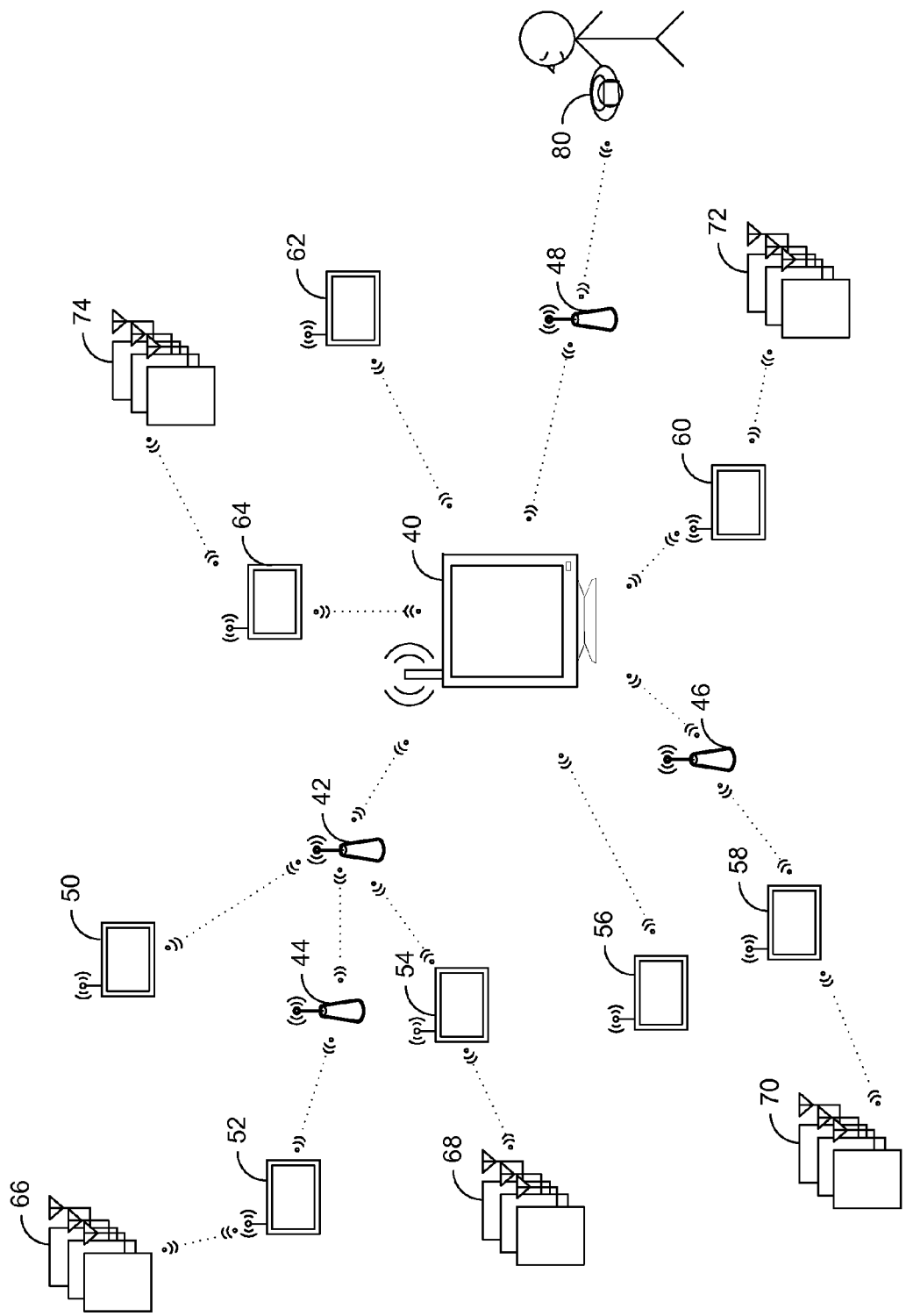
FIG. 2 illustrates a diagram of a patient monitoring system of the present invention for monitoring multiple patients.

FIG. 2 illustrates a diagram of a patient monitoring system of the present invention for monitoring multiple patients. For monitoring a group of patients, a monitor station 40, access points 42-48, bedside monitors 50-64, multiple sets of sensors 66-74 for multiple patients, and a portable monitoring device 80 can be connected together via wireless connections. The bedside monitors 50-64 are connected to the monitor station 40, either through a direct wireless connection with the monitor station 40 or via wireless communications with one or more of the access points 42-48. The access points 42-48 route the monitored data from the bedside monitors 50-64 to the monitor station 40, either directly or indirectly through other access points.

The bedside monitors 50-64 are available resources for the sensors 66-74 of the patients. Furthermore, each set of sensors is associated with measuring vital signs for a single patient. For instance, the sensors 66 can be associated to patient Z. Once associated to patient Z, the sensors 66 can be paired with one of the bedside monitors 50-64 at any time. Here, the sensors 66 can be paired to the bedside monitor 52 since the bedside monitor 52 may be the closest in proximity to the sensors 66.

The bedside monitor 52 can then communicate to any one of the access points 42-48. Since the access point 44 is nearest in proximity to the bedside monitor 52, the bedside monitor 52 can request the access point 44 to route the monitored data to the monitor station 40. If the access point 44 is available to accept the request from the bedside monitor 52, then the access point 44 wirelessly routes the monitored data to the monitor station 40 via a direct connection to the monitor station 40 or via another access point, e.g., via the access point 42.

Generally, a bedside monitor only monitors a single patient. Thus, sensors for other patients are not displayed on the bedside monitor since the beside monitor is already paired with the sensors of the single patient. When the bedside monitor is disconnected from the sensors of the single patient, then the bedside monitor can be used by other sensors of other patients or can go into a standby state. Therefore, a permanent or predefined coupling between bedside monitors and sensors is not required.

To keep track of the number and types of sensors for a patient, the sensors of a patient are grouped together and identified by the patient's identification number ("PID"). Using the above example with patient Z, the bedside monitor 52 can be coupled to patient Z by inputting patient Z's PID into the bedside monitor 52. The bedside monitor 52 can then connect to and look up a database (usually located at the monitor stations 40) to determine which sensors are associated with patient Z (in this example, sensors 66) and retrieve any passcodes to read the monitored data from the sensors 66. Thereby, the monitored data from the sensors 66 of patient Z can be received and displayed by the bedside monitor 52.

As a patient travels from one area to another area, the patient's PID can be inputted to a bedside monitor in the new area so that the beside monitor in the new area can communicate with and display the monitored data from the sensors. Once again using the above example with patient Z, patient Z is in a hospital room with the bedside monitor 52 located in the hospital room, where the bedside monitor 52 displays patient Z's vital signs on a screen of the bedside monitor 52. When patient Z moves to an operating room that has the bedside monitor 64, the hospital staff can input patient Z's PID into the bedside monitor 64 to initiate communicating with and displaying of patient Z's vital signs on the bedside monitor 64.

Since the monitor station 40 receives multiple vital signs and data from various patients, the monitor station 40 has a large data storage unit, e.g., an internal hard drive, for storing monitored data from various patients. The monitor station 40 can analyze and graphically display the stored monitored data for review and diagnose. The user interface of the monitor station 40 can display the monitored data for each patient on different areas, lines, and/or columns on the display screen of the monitor station 40. This overall display can give a brief overview of the patients' vital signs. However, the patient care provider can select anyone of the patients to display a more detailed display of that selected patient's vital signs.

Furthermore, if a patient care provider is providing care to more than one patient, then a portable monitoring device 80 can be selected to display any of the monitored data pertaining to the one of the patients. For instance, if an alert is received by the portable monitoring device 80 for a patient X, the portable monitoring device identifies and displays the location, type of alert, and the monitored data of patient X. Additionally, there can be multiple portable monitoring devices to monitor the patients, where each of the portable monitoring devices can be assigned to particular sets of patients.

The portable monitoring device 80 and the bedside monitor 52 can also receive various alarms issued by the monitor station 40 regarding patient Z. For instance, alarms can be issued in a pulse oximeter application, including the following alarms: (1) blood oxygen low alarm, when the blood oxygen value of a patient is below a low threshold value defined by a patient care provider; or (2) blood oxygen high alarm, when the blood oxygen value of a patient is above a high threshold value defined by a patient care provider.

In addition, one or more of the following alarms can be implemented: (1) heartbeat rate low alarm, when the heartbeat rate of a patient is below a low threshold heartbeat rate value defined by a patient care provider; (2) heartbeat rate high alarm, when the heartbeat rate of a patient is above a high threshold heartbeat rate value defined by a patient care provider; (3) no heartbeat alarm, when no heartbeat is detected from a patient; (4) battery low alarm, when the battery of a sensor is low; (5) sensor off alarm, when a sensor turns off; (6) sensor detached alarm, when a sensor is detached from a patient; (7) room temperature low alarm, when a room temperature is lower than a predefined low threshold of a target temperature range; (8) room temperature high alarm, when a room temperature is higher than a predefined high threshold of a target temperature range; (9) wireless connection lost alarm, when a wireless connection is lost; and (10) other alarms.

The monitor station checks the monitored data it receives from the bedside monitors, and issues alarms to the bedside monitor and/or portable monitoring device if one or more warning conditions are met. For the types of alarms, there are warning messages on the display, audio warning beeps, warning LEDs, and vibrations. The audio warnings can have multiple sounds types. For instance, the audio warnings can be three types, including the following types: a type 1 warning beep, which is a high-pitch short beep that repeats every half a second; a type 2 warning beep, which is a two second long beep that repeats after a short pulse/silent; and a type 3 warning beep, which is a high-pitch short beep that repeats every one minute.

There can also be priority among the various audio alarms. For instance, in the above example of having three types of audio alarms: type 1 is the highest priority; type 2 is the second priority; type 3 is the lowest priority. When multiple warnings happen, only the highest priority warning beep is played by the portable monitoring device. Generally, among the different alarms, the heartbeat rate warnings are type 1; the blood oxygen saturation warning is type 2; and all other warnings can be type 3. To stop the audio alarm, a patient care provider can press the alarm reset button of the bedside monitor or the monitor station. The alarm system can also be suspended for a predefined amount of time (e.g., five minutes) before it resumes.

Figure 3:
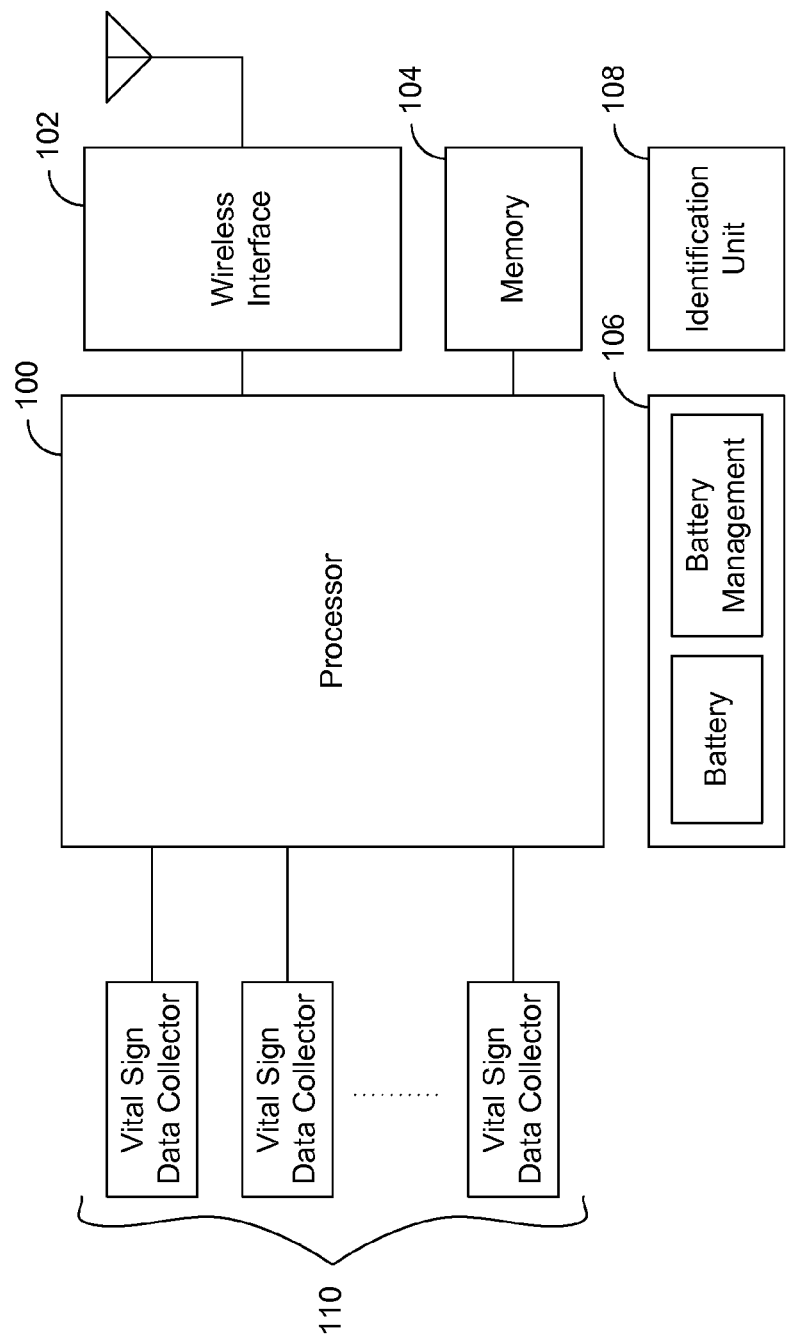
FIG. 3 illustrates a block diagram of a sensor of the present invention for sensing and processing a patient's vital signs.

FIG. 3 illustrates a block diagram of a sensor of the present invention for sensing and processing a patient's vital signs. A sensor comprises a processor 100, wireless interface 102, memory 104, battery unit 106, an identification unit 108, and vital sign data collectors 110. Memory can include various data storage technologies, including Flash memory, solid-state hard drive, random access memory ("RAM"), etc. The sensor is battery powered and can be comfortably attached to or worn by the patient. The wireless communication capability of the wireless interface 102 provides a wireless connection with a paired bedside monitor.

The identification unit 108 can be a radio-frequency identification ("RFID") device, a simple barcode, or other identification device used to identify the sensor to other devices, including the bedside monitor or the monitor station. For instance, if the identification unit 108 is an RFID device, then the RFID device will identify the sensor to any bedside monitors within the range of the RFID device. The RFID device can be used for identifying the sensor, the patient ID, and communication parameters for pairing with a bedside monitor.

The vital sign data collectors 110 can generate raw data for various vital sign measurements including an oxygen saturation of the patient, pulse rate of the patient, and other vital statistics. The processor 100 processes the raw data to generate the final vital sign measurements. Those measurements can be temporarily stored in the memory 104, before it is transmitted to the associated bedside monitor via the wireless interface 102.

In various embodiments of the present invention, a vital sign data collector can include a red LED, an infrared ("IR") LED, and a photo detector for pulse oximeter measurements, a temperature sensing element for measuring the patient's body temperature, or other hardware components for collecting raw data for certain vital signs. It is important to note that, depending on various implementations of the sensor, the number of vital sign data collectors for the sensor can vary. Thus, a single sensor can measure a single vital sign using a single data collector or measure multiple vital signs using multiple data collectors.

Figure 4:
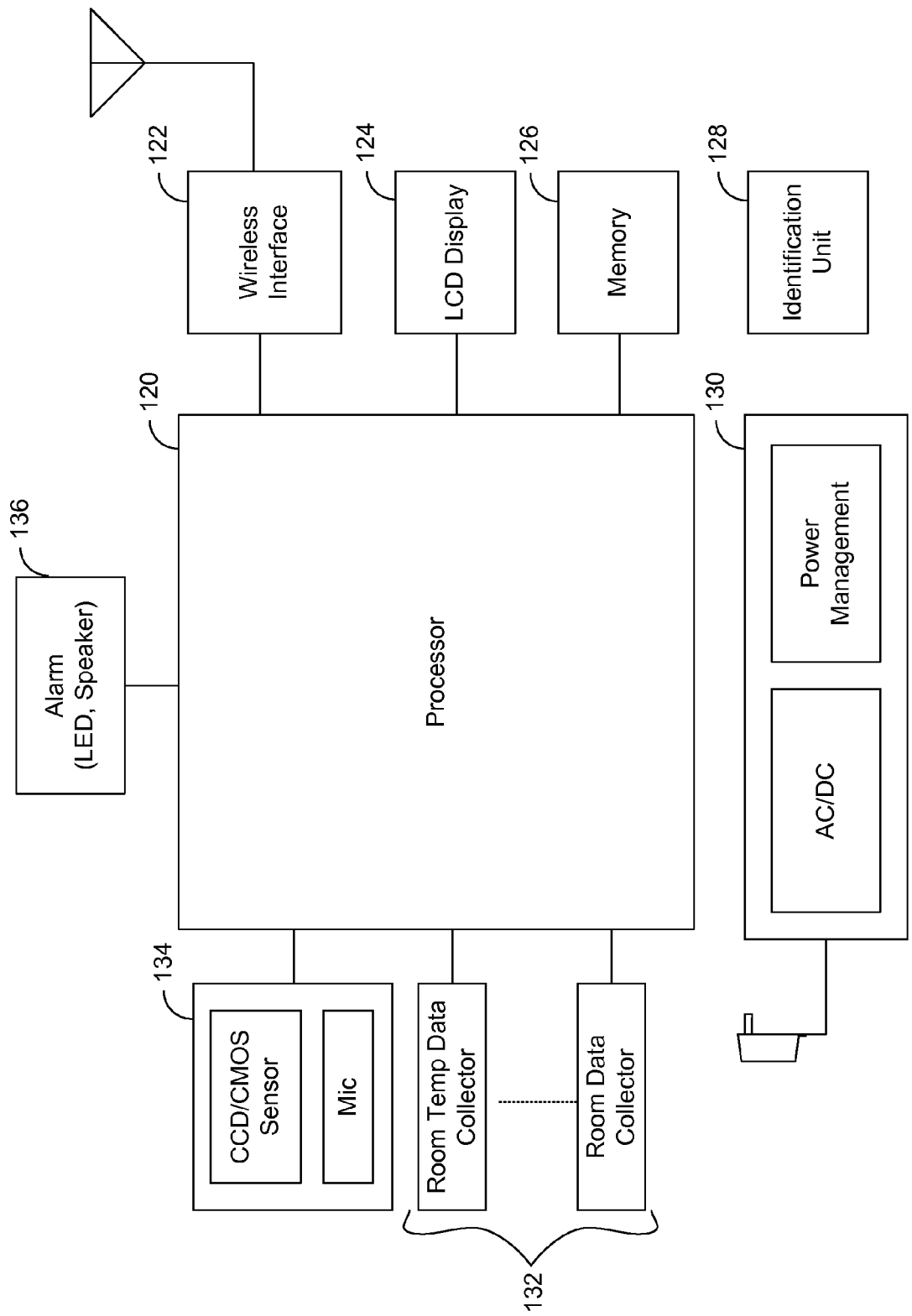
FIG. 4 illustrates a block diagram of a bedside monitor of the present invention.

FIG. 4 illustrates a block diagram of a bedside monitor of the present invention. A bedside monitor has the following components: (1) a processor 120, a wireless interface 122, an LCD display 124, memory 126, an identification unit 128, a power supply unit 130, room data collectors 132, audio/video recording unit 134, and an alarm 136. The bedside monitor has five main functions: (1) receiving and transmitting the monitored data from the sensors, including room conditions, to a remote monitor station; (2) live streaming of audio and video of the patient's activity; (3) measuring the environmental conditions; (4) signaling alarms; and (5) displaying the monitored data and system status.

Depending on the application, the video and audio streaming and the LCD display can be optional components of the bedside monitor. For example, for infant monitoring, the live video might be preferred; whereas for adult patient monitoring, it might not be acceptable due to privacy concerns of the patient. In addition for hospital monitoring, the LCD display might be preferred since the patient care providers can read the status of the patient by simply viewing the LCD display. In home care applications, the LCD monitor may not be needed, e.g., in home infant monitoring, it can be omitted.

In the preferred embodiments of the present invention, the bedside monitor uses a long range wireless communication protocol, e.g., Wi-Fi. Thus, the bedside monitor is designed to receive power from an alternating current ("AC") power plug, connected to the wall outlet, or a sizable rechargeable battery. Furthermore, due to video streaming requirements, a high bit rate wireless transmission is required. Appropriate current art technologies are available for possible solution to the wireless communication and high bit rate requirements.

The processor 120 packs the monitored data, including the audio and video data, the vital sign data, and room condition data into packages, then encrypts the monitored data, and transmits the monitored data via the wireless interface 122 to the monitor station. When an LCD screen is available, the processor 120 displays the monitored data, the system status, and any warning messages on the LCD screen. When directed by the monitor station, the processor 120 can also activate the alarm 136.

For monitoring multiple patients, the identification unit 128 can be a barcode/RFID reader designed to easily pair the bedside monitor to the sensor without having to connect any wires to the sensor. Once pairing is completed, the bedside monitor receives and displays the monitored data from the paired sensor.

Figure 5:
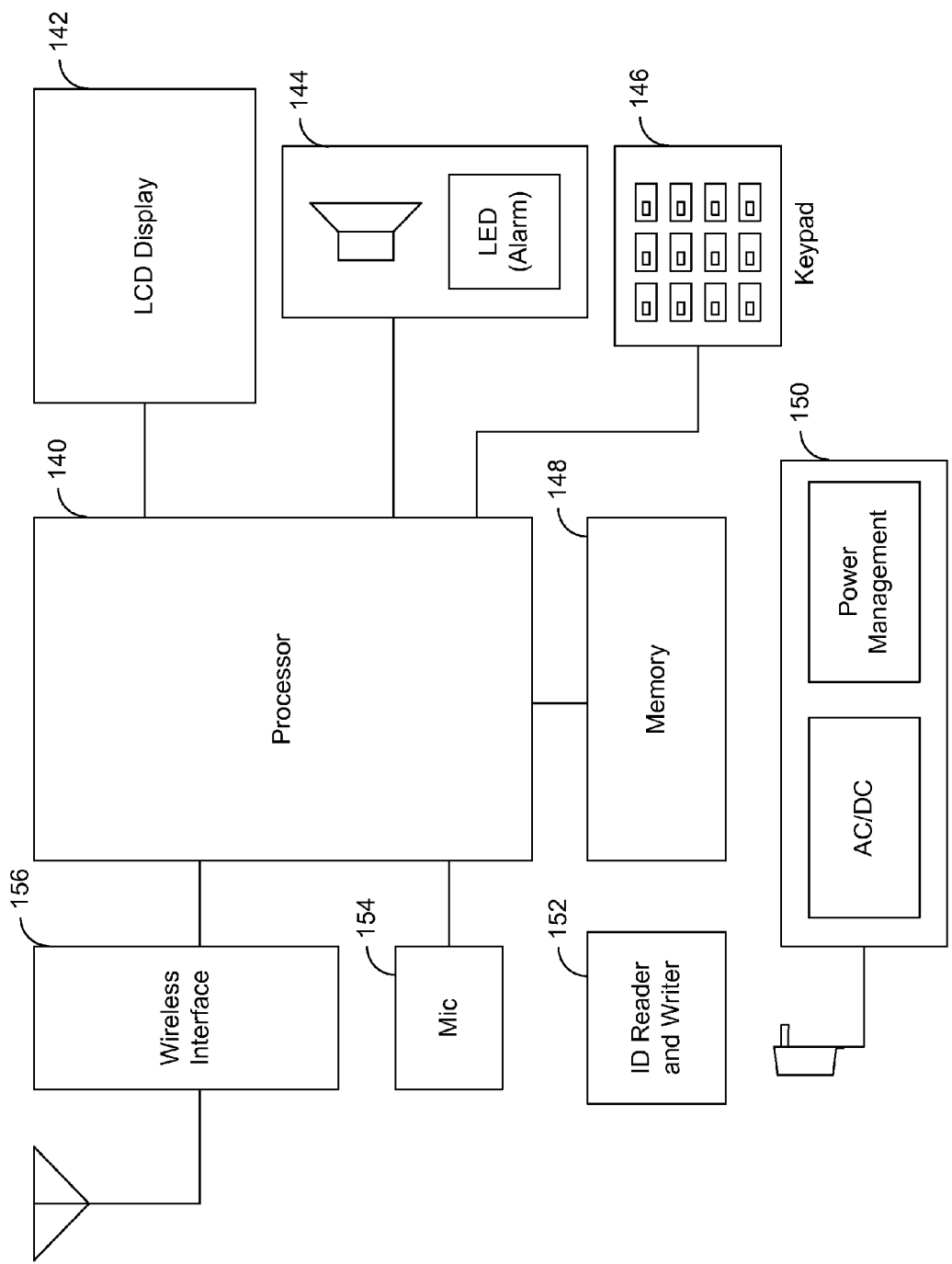
FIG. 5 illustrates a block diagram of a monitor station of the present invention.

FIG. 5 illustrates a block diagram of a monitor station of the present invention. A monitor station comprises a processor 140, a wireless interface 156, an LCD display 142 (or a touch screen LCD display), an alarm 144, memory 148, a keypad 146, a power supply unit 150, an ID reader 152 (e.g., a barcode reader or an RFID), and a microphone 154. The monitor station continuously monitors the patient's vital signs and the room conditions. When a touch screen LCD display is used, then keypad 146 can be omitted since the touch screen LCD can provide the functionality of a keypad.

The patient's monitored data is received by the wireless interface 156. Once the monitored data is received, the processor 140 displays the monitored data and the system status on the LCD screen 142. The monitored data can also be stored in the memory 148 for future recall and review. The processor 140 checks the data against any present alarm conditions. The alarm conditions are programmable and can be set by the user via the keypad or the graphic user interface ("GUI") in the touch screen.

When one or more certain preset conditions are met, an alarm is activated. The alarm can be sent to the LCD display 142 and a portable monitoring device to inform the patient care provider of the alarm. When the patient care provider has the portable monitoring device, the monitor station broadcasts the patient's encrypted monitored data and system status to the portable monitoring device. The alarm can be transmitted to the correct portable monitoring device since the monitor system identifies which sensors are assigned to which patient by pairing the patient's data with the sensors assigned for that patient. Furthermore, the portable monitoring unit can be associated with certain patients to receive alarms for those certain patients. A unique patient ID is assigned to the patients, such that their patient's data and information can be easily retrieved from a database. The unique patient ID can be implemented by a barcode, a RFID, or other type of technology for identification.

Also, a computing device with the appropriate application software and a wireless receiver can receive the broadcasted monitored data from the monitor station and store the data in the local storage device such as a hard disk or memory stick. The application software can then retrieve, analyze, and display the monitored data for review.

Figure 6:
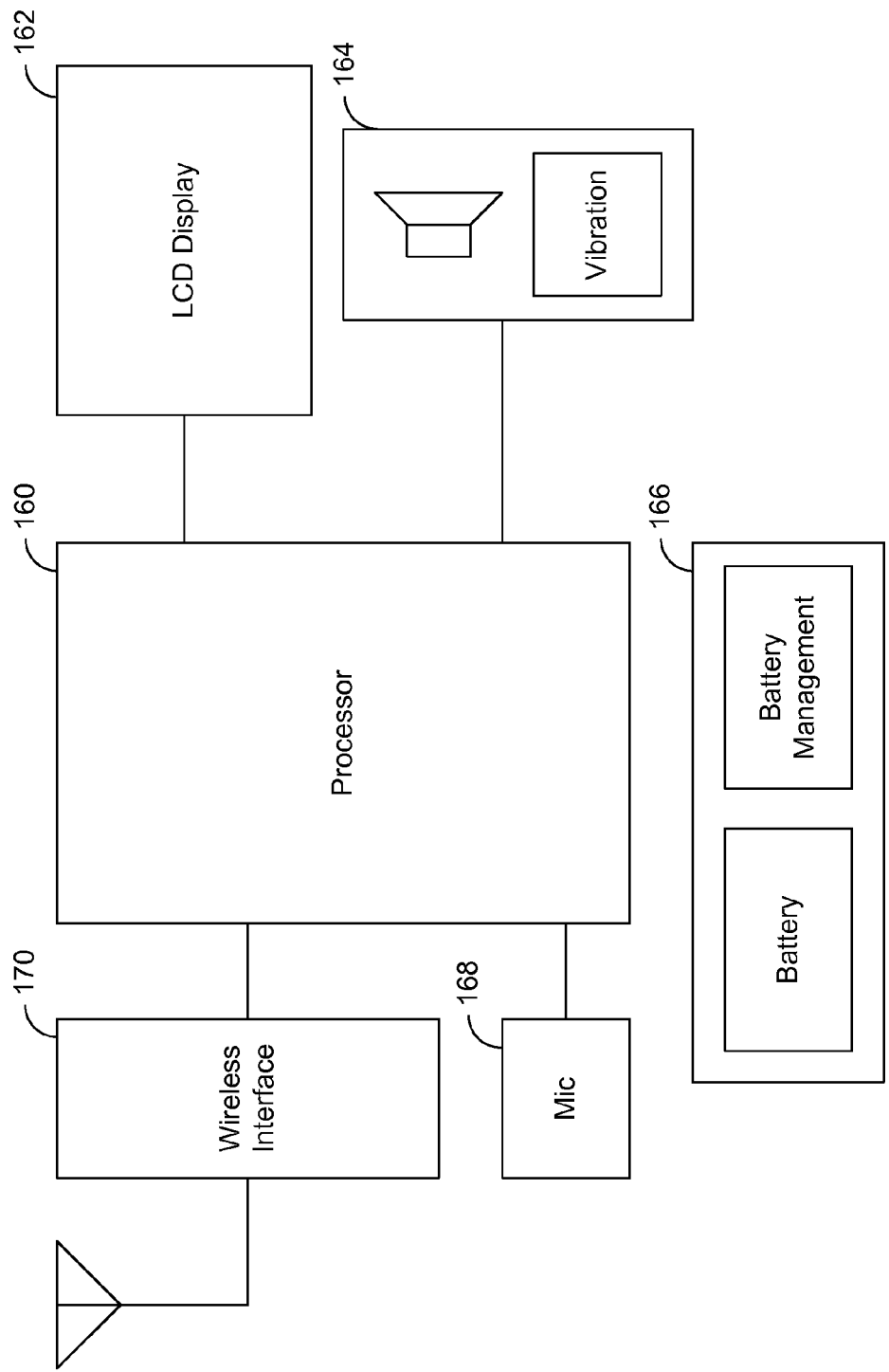
FIG. 6 illustrates a block diagram of a portable monitoring device of the present invention.

FIG. 6 illustrates a block diagram of a portable monitoring device of the present invention. A portable monitoring device comprises a processor 160, a wireless interface 170, an LCD display 162, an alarm 164, a power supply unit 166, and a microphone 168. The portable monitoring device can be worn or otherwise carried by a health care provider and can be designed to have low power consumption of the power supply unit 166. The portable monitoring device listens to the broadcast from the monitor station and can update its LCD display with any received data from the monitor station. Due to the lower power requirement, the LCD display can turn off or otherwise go into a sleep mode after a preset amount of time has lapsed. When the portable monitoring device is in use, the LCD display 162 can be turned on for user operation. When an alarm is received, the alarm 164 vibrates the portable monitoring device or produces a beeping sound (or both) to alert the patient care provider. The mode of the alarm can be set by the user.

Figure 7:
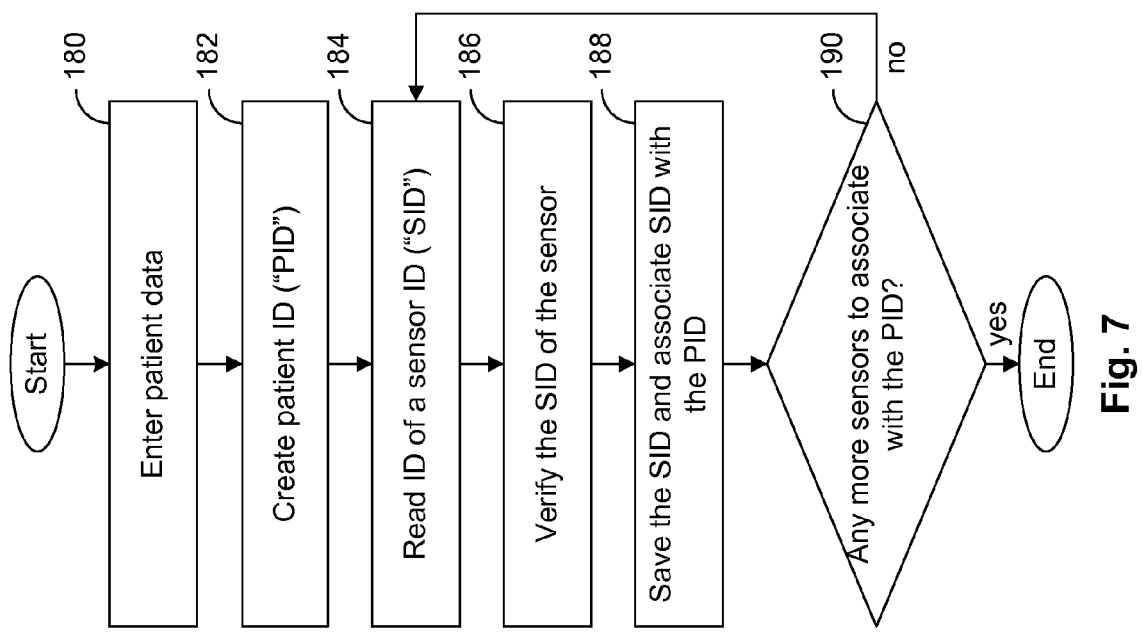
FIG. 7 illustrates a flowchart for registering a patient in a patient monitoring system of the present invention.

FIG. 7 illustrates a flowchart for registering a patient in a patient monitoring system of the present invention. A new patient's data and his/her sensors are associated to each other so the monitor station can determine which patient's monitored data it is receiving. To register a new patient, the patient's data is entered 180, including the patient's name, age, social security number, etc. A unique patient ID is then created for the patient 182. The patient ID is then encrypted and stored in a patient ID tag in the form of a barcode, a RFID, or another technology for identification. The patient ID tag can be worn on the wrist of the patient during hospitalization.

Once the patient is logged in to the monitor station, an ID reader of the monitor station scans the ID of a sensor 184 to use on the patient. A barcode or RFID of a sensor contains encrypted data for the sensor ID, serial number, or other private data, including a key or passcode for communication setup. The patient ID, the sensor ID, and the patient's data are grouped together and stored in the storage device of the monitor station (or other storage device remote or local to the monitor station). The sensor ID is verified 186 and the sensor ID is saved and linked to the patient ID 188. If there are any more sensors to scan 190, then a next SID of the next sensor is read to be an associated with the PID until no more sensors are left to be read for that patient.

Figure 8:
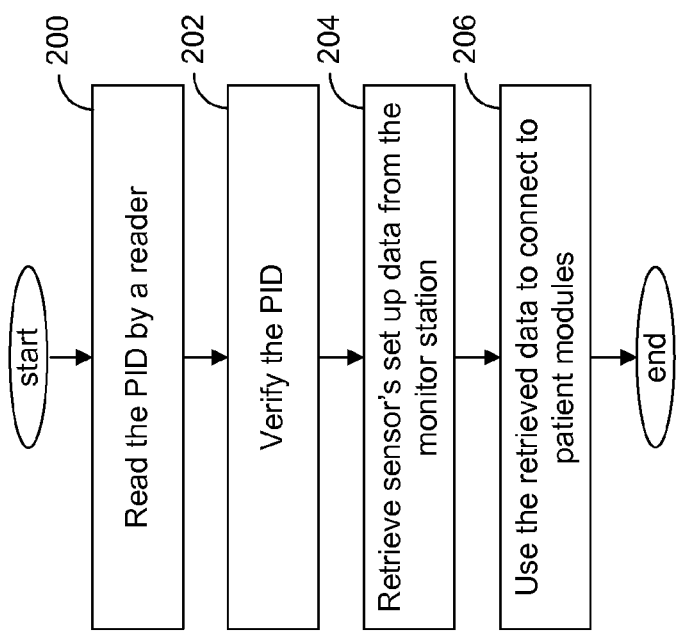
FIG. 8 illustrates a flowchart for pairing a bedside monitor with a sensor.

FIG. 8 illustrates a flowchart for pairing a bedside monitor with a sensor. After registering the patient and the sensors, the sensors need to be paired with a bedside monitor. Once paired, the patient's vital sign data can be displayed on the screen of the bedside monitor. The bedside monitor also transmits the monitored data from the patient to the monitor station. In order to pair the bedside monitor and the sensors, the identification reader can read the encrypted patient ID 200, e.g., the patient's ID tag, worn on the wrist of the patient can be read by a bar code scanner to scan the barcode given to the patient. Next, the patient ID is verified by the monitor station as to whether the patient ID is valid 202. If it is valid, the patient ID is stored for future communication with the monitor station. The sensors' set up data is then retrieved from the monitor station 204, so that the bedside monitor can set up communications with the sensors. The pairing processes between the bedside monitor and the sensors can then be completed using the information retrieved via the monitor station 206. After pairing is completed, the bedside monitor will (1) start receiving the monitored data from the sensors, (2) display the monitored data on its screen, (3) pack the monitored data and the patient ID into a data package, (4) encrypt the data package, and (5) send the encrypted data package to the monitor station.

Figure 9:
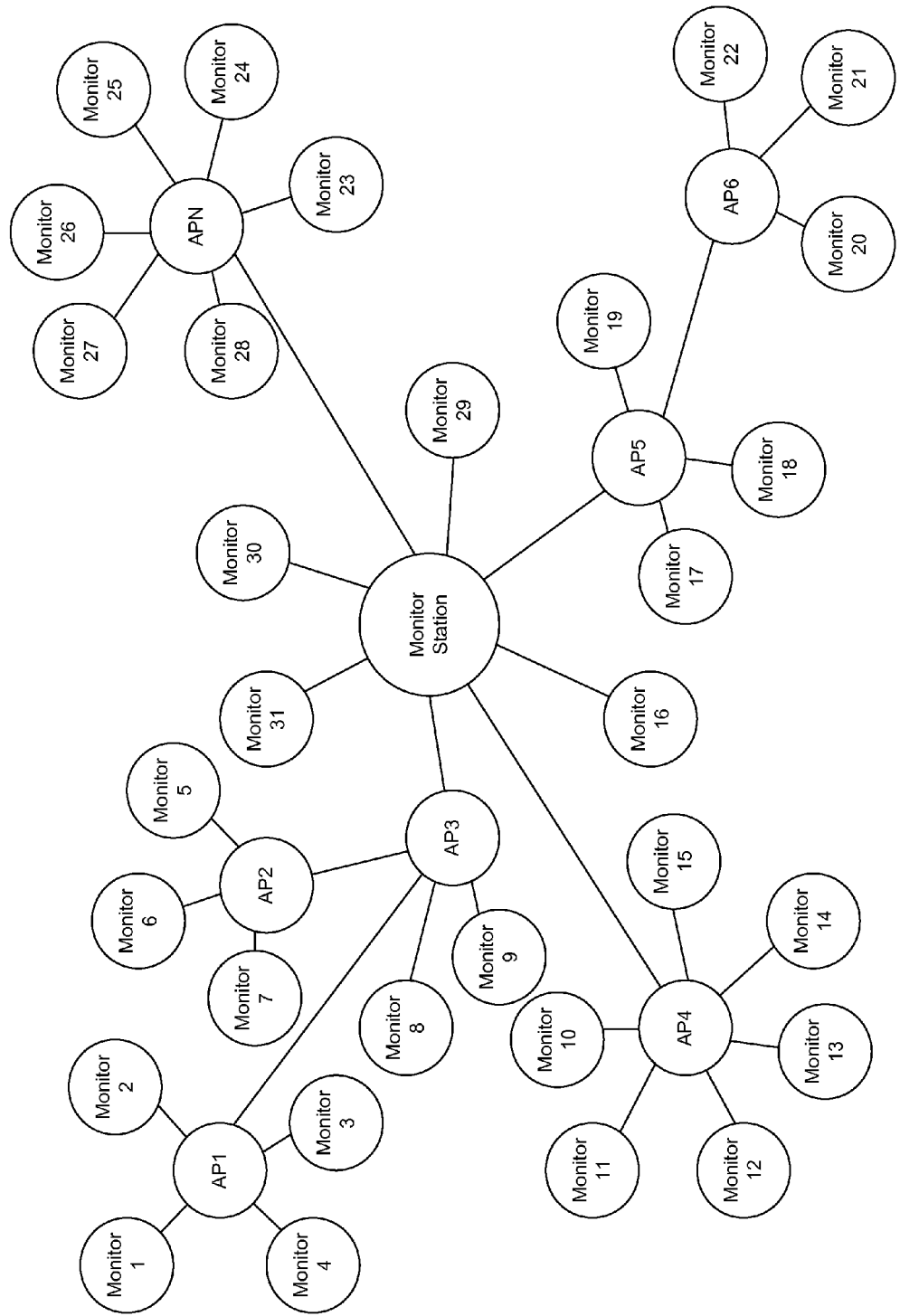
FIG. 9 illustrates a network topology of a patient monitoring system for monitoring multiple patients.

FIG. 9 illustrates a network topology of a patient monitoring system for monitoring multiple patients. The network topology can have a tree topology, where the monitor station is at the center/top of the tree. Around the monitor station, there are bedside monitors 1-31 and access points 1-N in a star shape connection. A bedside monitor can directly connect to the monitor station if it is within the wireless range of the monitor station. For instance, bedside monitor 16, bedside monitor 29, bedside monitor 30, and bedside monitor 31 are within range of the monitor station, so these bedside monitors 16, 29, 30, and 31 can directly connect with the monitor station.

If a bedside monitor is not within range of the monitor station, that bedside monitor can connect to a nearby access point to have its monitored data routed to the monitor station via a network connection. An access point can also connect to the monitor station via one or more other access points. Thus, in an embodiment of the present invention, the bedside monitors and the access points are connected in a star shape topology. When an access point has reached a maximum capacity of connections to bedside monitors, any additional bedside monitors can be redirected to the next nearby access point to route the monitored data to the monitor station.

Since connections between sensors, bedside monitors, access points, and the monitor stations are not fixed, the network topology can be dynamic. Access points and bedside monitors can be disconnected from any existing connections, and be reconnected to a different access point. For example, in a hospital application, bedside monitors may be scattered throughout the hospital, where each hospital room has one bedside monitor fixed to that room. Thus, if a patient Y moves from a room that has bedside monitor 1 to an operating room that has bedside monitor 25, the patient's sensors are initially paired to bedside monitor 1. When patient Y reaches the operating room, the sensors of patient Y are paired and wirelessly connected to bedside monitor 25, so that bedside monitor 25 can display the vital signs for patient Y. Bedside monitor 1 may also lose its connection due to the sensors of patient Y being out of communication range from bedside monitor 1 or can be otherwise disconnected since the patient is no longer in the respective room of bedside monitor 1.

In other embodiments of the present invention, the bedside monitor for a patient can travel with the patient as it navigates through the hospital. For instance, in the previous example, monitor 1 can travel wherever patient Y goes. As patient Y is navigating through the hospital, bedside monitor 1 can search for nearby access points or the monitor station to transmit the monitored data of patient Y to the monitor station.

Figure 10:
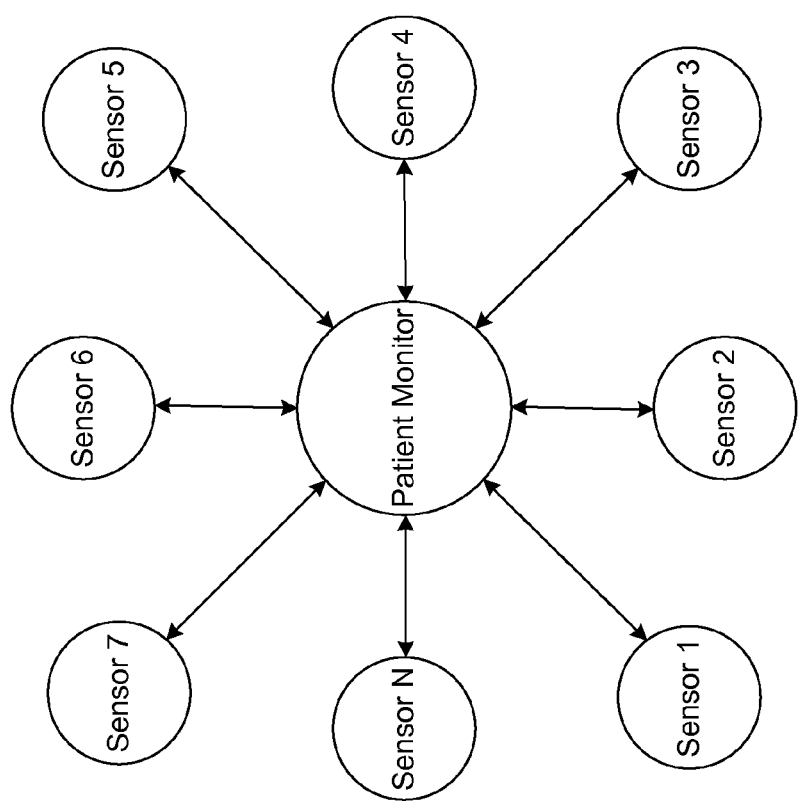
FIG. 10 illustrates a network topology of a bedside monitor communicating with multiple sensors.

FIG. 10 illustrates a network topology of a bedside monitor communicating with multiple sensors. The connection topology between a bedside monitor and the sensors of a single patient can resemble a star topology. The bedside monitor can be paired to the sensors of the patient. Typically, the bedside monitor can only service one patient and that patient's sensors at any given time. Thus, other sensors of other patients cannot connect with the bedside monitor until the bedside monitor is released or otherwise disconnected from the occupying patient.

FIG. 11 illustrates a data format for a data package for sensor setup information that is transmitted to a bedside monitor. In order for a bedside monitor to connect and receive data from a sensor, the sensor must receive setup information for the sensor. That information is delivered to the bedside monitor by the monitor station in a data package that generally has the following data fields: sensor identification ("SID"), sensor class, passcode, encryption key, reserved portion, and error detection. The SID is a unique alphanumeric number to distinguish each sensor from other sensors. The sensor class represents the type of sensor, such as an oximeter, temperature sensor, ECG sensor, etc. The passcode is the setup parameter to set up the communication channel between the sensor and the bedside monitor during the pairing phase. The encryption key is the key for encrypting/decrypting the data packages from the sensor. There can also be several bytes reserved for any other uses. At the end of the package is data for error detection, e.g., cyclic redundancy check ("CRC"), to ensure the integrity of the package.

FIG. 12 illustrates a data format for a data package that is transmitted from a sensor to its paired bedside monitor. Once a sensor and a bedside monitor are paired, then the sensor can begin sending its sensor readings to the bedside monitor. The sensor readings are generally packaged into a data package that has the following fields: SID, sensor class, package number, data type, data length, data0, data1, . . . dataN, and CRC. The SID and the sensor class are used to uniquely identify the sensor.

Each of the data packages has a package number to identify the order of the data packages. For instance, the package number can increase sequentially (or otherwise vary the package number in some order) for every additional data package transmitted by the sensor. When the bedside monitor or the monitor station receives two data packages with the same package number, one of the data packages is dropped since the data packages are duplicative of each other. When the package numbers of two consecutive data packages are not consecutive numbers, this implies that a data package was lost.

The data type represents what kind of data, such as blood oxygen saturation, heartbeat rate, blood pressure, etc. is in the data package. The data length is the total bytes of data in the data package. The data contents are Data0, . . . , DataN. The data type, data length, Data0, . . . , DataN are encrypted by the sensor's private key before the data package is transmitted to the bedside monitor or the monitor station. The bedside monitor or the monitor station can decrypt the data package with the encryption key for that sensor.

FIG. 13 illustrates a data format for a data package transmitted from a bedside monitor to a monitor station. Upon receiving a data package from a sensor, the bedside monitor first checks the SID, and sensor class to see if the data package is from one of the paired sensors. If not, the bedside monitor discards the package. If the data package is from one of the paired sensors, the bedside monitor verifies the package number to see if the package is new. If not, the package is discarded; if yes, the package is decrypted and the data from the package is displayed on the bedside monitor (if the bedside monitor has a display). The bedside monitor can then package its ID (the bedside monitor ID, "MID"), a time stamp, and the patient ID at the beginning of the data package to form a new data package. The new data package is encrypted and transmitted to the monitor station for further processing.

Figure 14:
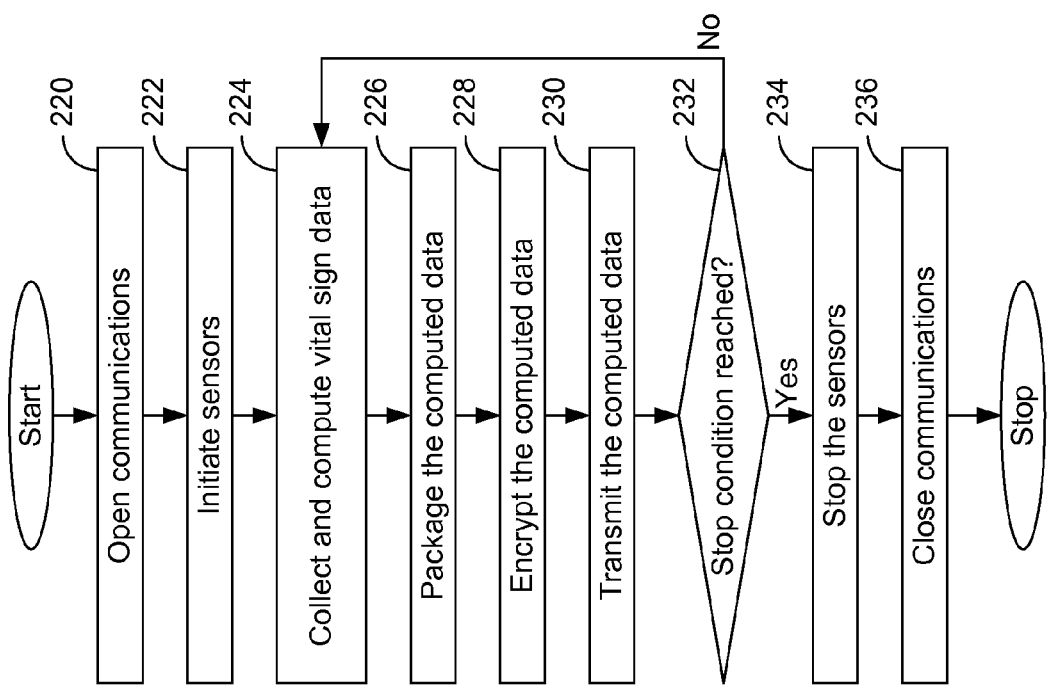
FIG. 14 illustrates a flowchart for operating a sensor.

FIG. 14 illustrates a flowchart for operating a sensor. When a sensor is powered on, the embedded processor of the sensor first initializes the wireless communication and then activates the attached sensors. During the initialization of the wireless communication, a communication channel is opened 220 to pair sensors with a bedside monitor. The sensors are then initialized 222. After initialization, the sensors are controlled to collect, measure, and compute the vital sign data from the patient 224. Generally, the sensor computes the vital sign data from the measured raw data. The vital sign data is then packaged 226, where the data in the package is encrypted 228. The package is then transmitted 230 to the bedside monitor for display and/or transmittal to the monitor station.

Next, the patient sensor determines whether a stop condition exists 232, if yes, then the sensor are stopped from taking measurements 234 and the communication with the bedside monitor is closed 236. One of the stop conditions can be whether there is enough power to continue with another set of measurements, whether the sensor is turned off, whether the sensor is no longer connected to the patient, or other condition for stopping the vital sign measurements of the patient. If the sensor does not stop, then it loops back to the collecting, measuring, and computing the vital sign data step 224 until a stop condition is reached.

Figure 15:
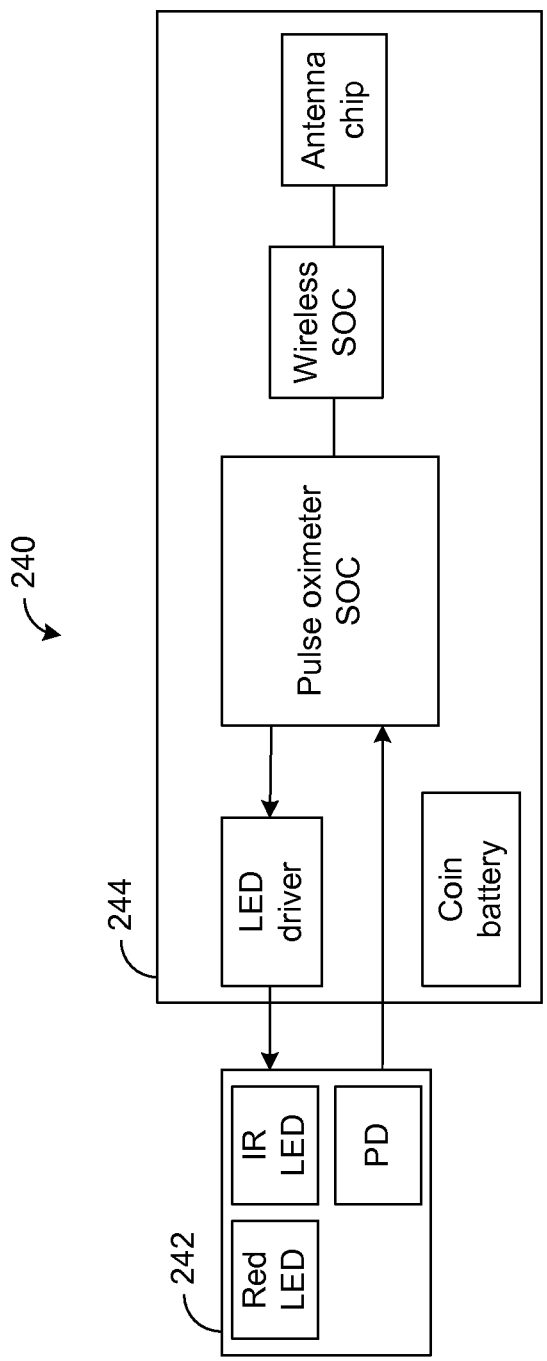
FIG. 15 illustrates a block diagram of a sensor for measuring blood oxygen saturation ("SpO2") and pulse rates with a built-in battery onboard.

FIG. 15 illustrates a block diagram of a sensor for measuring blood oxygen saturation and pulse rates with a built-in battery onboard. In an embodiment of the present invention, a sensor is a pulse oximeter 240. The pulse oximeter 240 comprises a vital sign data collector 242 and a patch 244. The vital sign data collector 242 includes a red LED, an infrared LED, and a photodiode ("PD"). The patch 244 includes a LED driver, a coin battery, a pulse oximeter system-on-chip ("SOC"), a wireless SOC, and an antenna chip.

A cable can be used to connect the vital sign data collector 242 and the patch 244 together. The coin battery is on board the patch 244 to power the patch 44 and the vital sign data collector 242. The patch 244 can attach to and detach from the vital sign data collector 242 via a connector (not shown) on the patch 244. The connector of the patch 244 can be implemented by various technologies, e.g., the connector can be a universal serial bus ("USB"), mini-USB, or other electronic interface technology. One of the benefits of having the vital sign data collector 242 and the patch 240 detachable is that the vital sign data collector 242 can be replaced with a new vital sign data collector.

Figure 16:
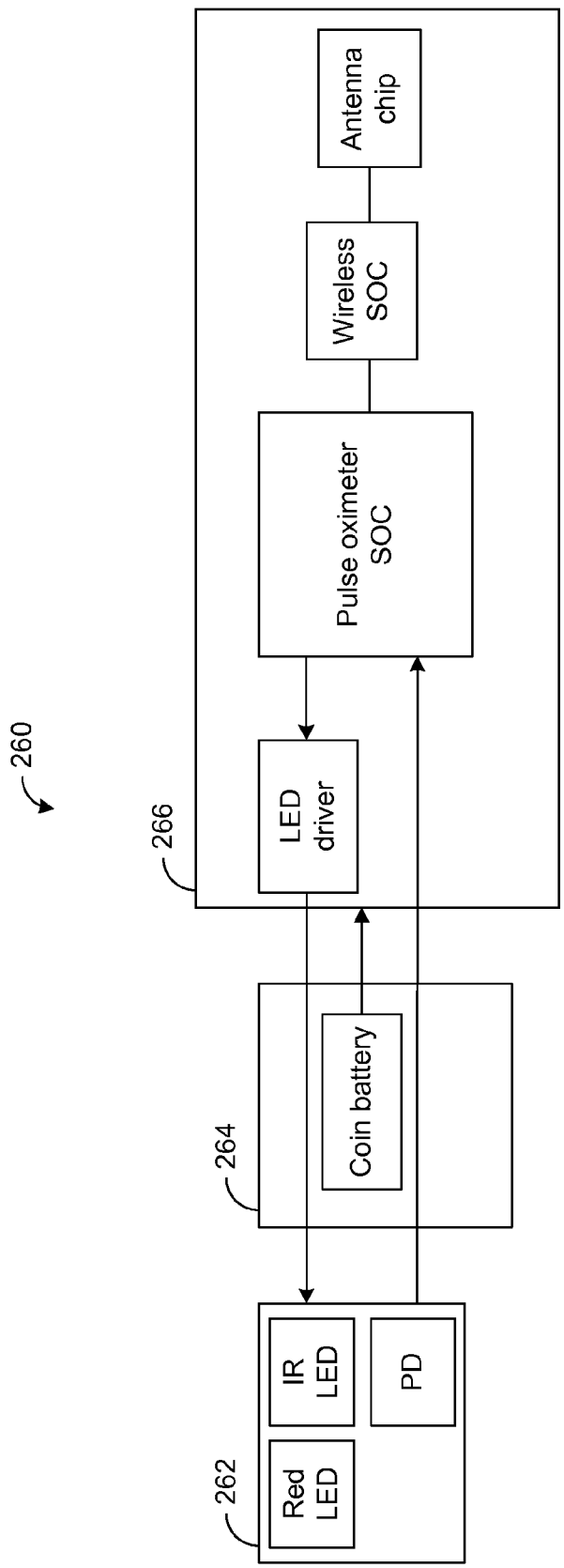
FIG. 16 illustrates a block diagram of a sensor for measuring blood oxygen saturation and a pulse rate with a detachable battery board and sensor.

FIG. 16 illustrates a block diagram of a sensor for measuring blood oxygen saturation and a pulse rate with a detachable battery board and vital sign data collector. In an embodiment of the present invention, a sensor is a pulse oximeter 260. The pulse oximeter 260 comprises a vital sign data collector 262, a battery board 264, and a patch 266. Here, the coin battery is not located on the patch 266. Rather, the battery board 264 holds the coin battery and passes connecting wires between the patch 266 and the vital sign data collector 262. A cable can be used to connect the vital sign data collector 262 and the battery board 264. And another cable can connect the battery board 264 to the connector of the patch 266. Therefore, the battery board 264 and the vital sign data collector 262 are attachable to and detachable from the patch 266. In this configuration, the battery board 264 and the vital sign data collector 262 can be disposed of after the battery on the battery board 264 is depleted or for other reasons.

The vital sign data collector 262 contains a red LED, an IR Led and a PD. A sensor holder (not shown) is designed to connect the sensor to an area of the patient for measurement, such as the finger, the toes, ears, etc. The patch 266 contains a LED driver, a pulse oximeter SOC (i.e., a processor), a wireless SOC and an antenna chip. The LED driver provides the electric current to drive/turn on and off the LEDs by the control of the pulse oximeter SOC.

During a pulse oximetry measurement, the red LED and IR LED are turned on one at a time. When one of the LEDs is on, the PD collects the light that passes through from the measured area of the patient. The pulse oximeter SOC then collects the raw data from the output of a D/A (Digital-to-Analog) converter of the PD. The pulse oximeter SOC continues switching on the red LED and IR LEDs one by one in sequence until sufficient data points are collected. Then, the pulse oximeter SOC computes the SpO2 value by filtering and other required mathematical formulas on the data. The pulse oximeter also adjusts the power of the LEDs, as needed.

Once a set of data is obtained, the data is packed and encrypted. The data is then sent to the wireless SOC to transmit to the paired bedside monitor. Short range wireless communication is used to conserve power consumption by the sensor. A number of available wireless sensor network technologies can be used for this purpose, e.g., the Bluetooth, ZigBee, ANT, or other wireless technologies. When shuttering down the sensor, the sensor is stopped and the wireless communication to the bedside monitor is disconnected.

Figure 17:
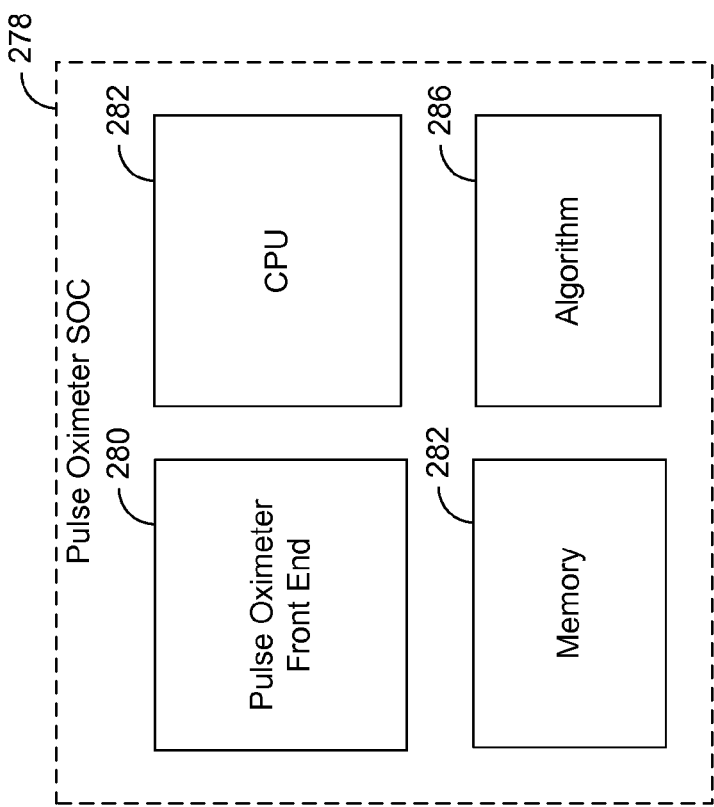
FIG. 17 illustrates a block diagram of a pulse oximeter system-on-chip ("SOC").

FIG. 17 illustrates a block diagram of a pulse oximeter system-on-chip ("SOC"). A pulse oximeter SOC 278 contains a pulse oximeter front end 280, memory (e.g., flash or RAM) 284, a software algorithm 286, and a processor ("CPU") 282. The pulse oximeter front end 280 controls the power of the LEDs, switches the LEDs between on and off, and performs data collection.

Figure 18:
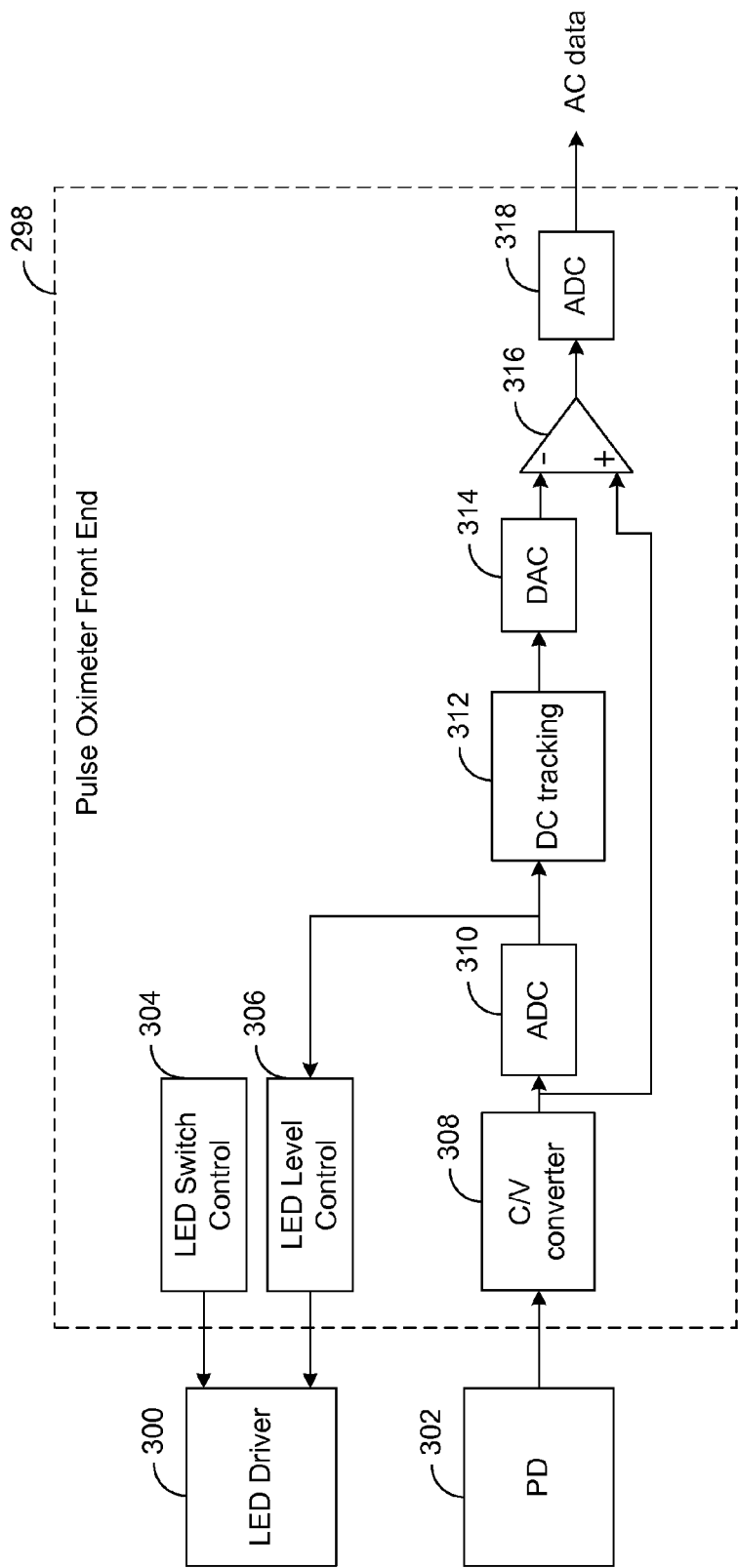
FIG. 18 illustrates a block diagram of the front end processing for a pulse oximeter of the present invention.

FIG. 18 illustrates a block diagram of the front end processing for a pulse oximeter. For a pulse oximeter front end processing 298, a LED level control 306 adjusts the output power of a red LED and an IR LED of the pulse oximeter via an LED driver 300 based on an output reading from a PD 302. An LED switch control 304 turns on and off the LEDs by the command of a CPU, When the PD 302 receives light energy, it generates a reverse light current. The reverse light current is then magnified and converted to a voltage by a current-to-voltage converter ("C/V converter") 308. The voltage is inputted to an analog-to-digital converter ("ADC") 310 to convert the voltage to a digital number for processing by the CPU. The CPU applies a direct current ("DC") tracking filter 312 to estimate/track the DC component of the raw data. A DC tracking filter can be a low pass filter or other known filters can also be used. For example, a popular digital filter of the DC tacking filter is defined by the mathematical equation $$y[n]=K \cdot x[n]+(1-K) \cdot y[n-1], \tag{1}$$

where $x[n]$ and $y[n]$ are the input and the output of the DC tracking filter at the sampling time instance n, respectively; $y[n-1]$ is the previous output of y; and K is a constant/gain for the filter. The constant K is a small number to control the rate of tracking, where its value can be obtained by experiment. For an oximeter application, the constant K can be $\frac{1}{2}^9$.

Once the DC component is computed, the DC value is converted into an analog signal by a digital-to-analog converter ("DAC") 314. The voltage output from the C/V converter 308 is inputted to the positive input of an OP amplifier 316 and the tracked DC signal from the DAC 314 is inputted to the negative input of the OP amplifier 316. The output of the OP amplifier 316 is the amplified AC component of the original voltage output from the C/V converter 308. The amplified AC component is then digitized by an ADC 318. Therefore, the output of the pulse oximeter front end 280 is the amplified AC digital data of the output of the PD 302.

Figure 19:
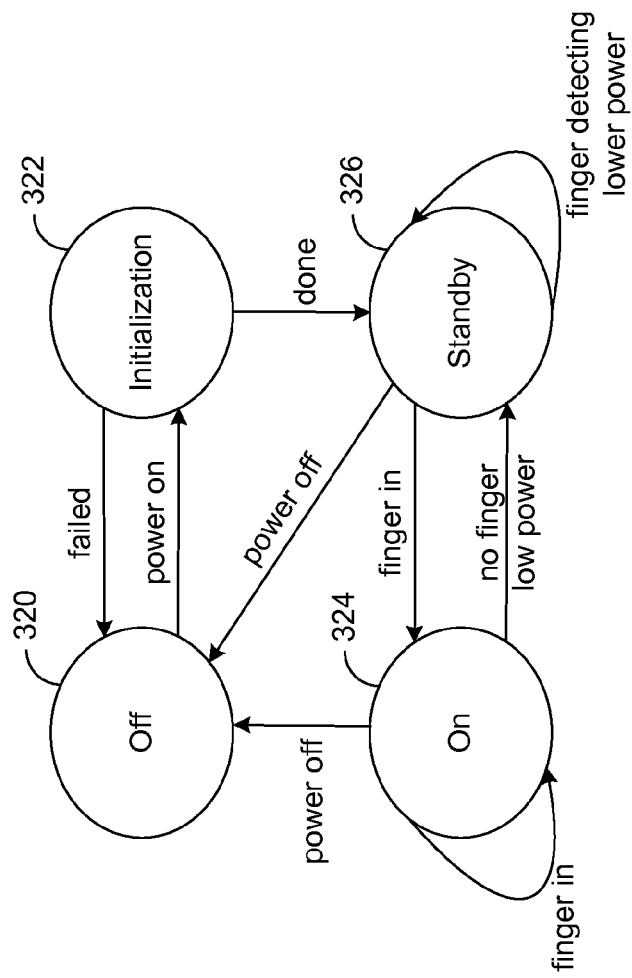
FIG. 19 illustrates a state diagram of pulse oximeter states.

FIG. 19 illustrates a state diagram of a pulse oximeter states. The operations of a pulse oximeter can be divided into the following states of an off state 320, an initialization state 322, an on state 324, and a standby state 326. The pulse oximeter can transition from one state to another. In the off state 320, the pulse oximeter is powered off and has no activity. Once powered on, the pulse oximeter goes to the initialization state 322 that initializes the wireless communication to the paired bedside monitor, sets up the CPU internal registers and timers, executes the initialization procedures of the software, etc. If the initialization is successful, the pulse oximeter goes to the standby state 326.

In the standby state 326, the oximeter repeatedly detects if the patient's body, e.g., a finger, toe, earlobe, or other body part, is connected to the sensor in order for the sensor to measure the vital signs of the patient. For instance, if the sensor has is clipped to a person's fingers, then the pulse oximeter will detect whether or not the person's finger is clipped in to the sensor. If the pulse oximeter detects the finger, the state changes from standby 326 to the on state 324. In the on state 324, the pulse oximeter continuously measures the blood oxygen saturation and the heartbeat rate by pulsing the LEDs of the pulse oximeter and receiving data from the PD of the pulse oximeter. When the finger is out or otherwise removed from the sensor, the pulse oximeter goes back to the standby state 326. When the pulse oximeter is powered off, the pulse oximeter goes to the off state 320. If the power of the pulse oximeter is low, the pulse oximeter goes to the standby state 326 until power is depleted.

Figure 20:
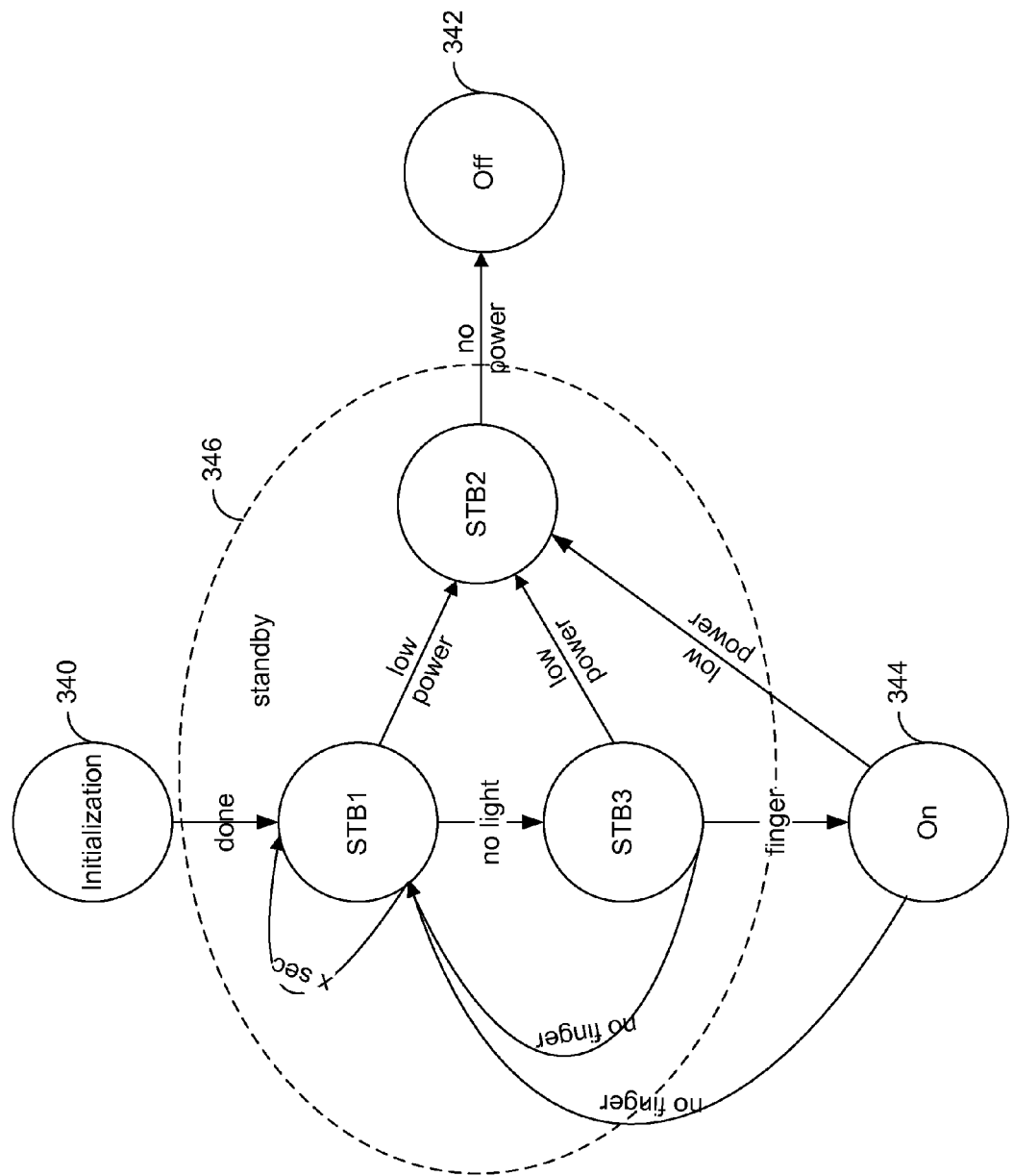
FIG. 20 illustrates a state diagram of various standby state transitions of a pulse oximeter.

In other embodiments of the present invention, the standby state 326 can be further divided into multiple standby states. FIG. 20 illustrates a state diagram of various state transitions of multiple standby states. In this example, there are three standby states STB1, STB2, and STB3 346. The three standby states 346 can transition from one to another and from the other states of a pulse oximeter, including an initialization state 340, an off state 342, and an on state 344. The details with respect to transitioning between the various states are explained in detail with respect to FIG. 21.

Figure 21:
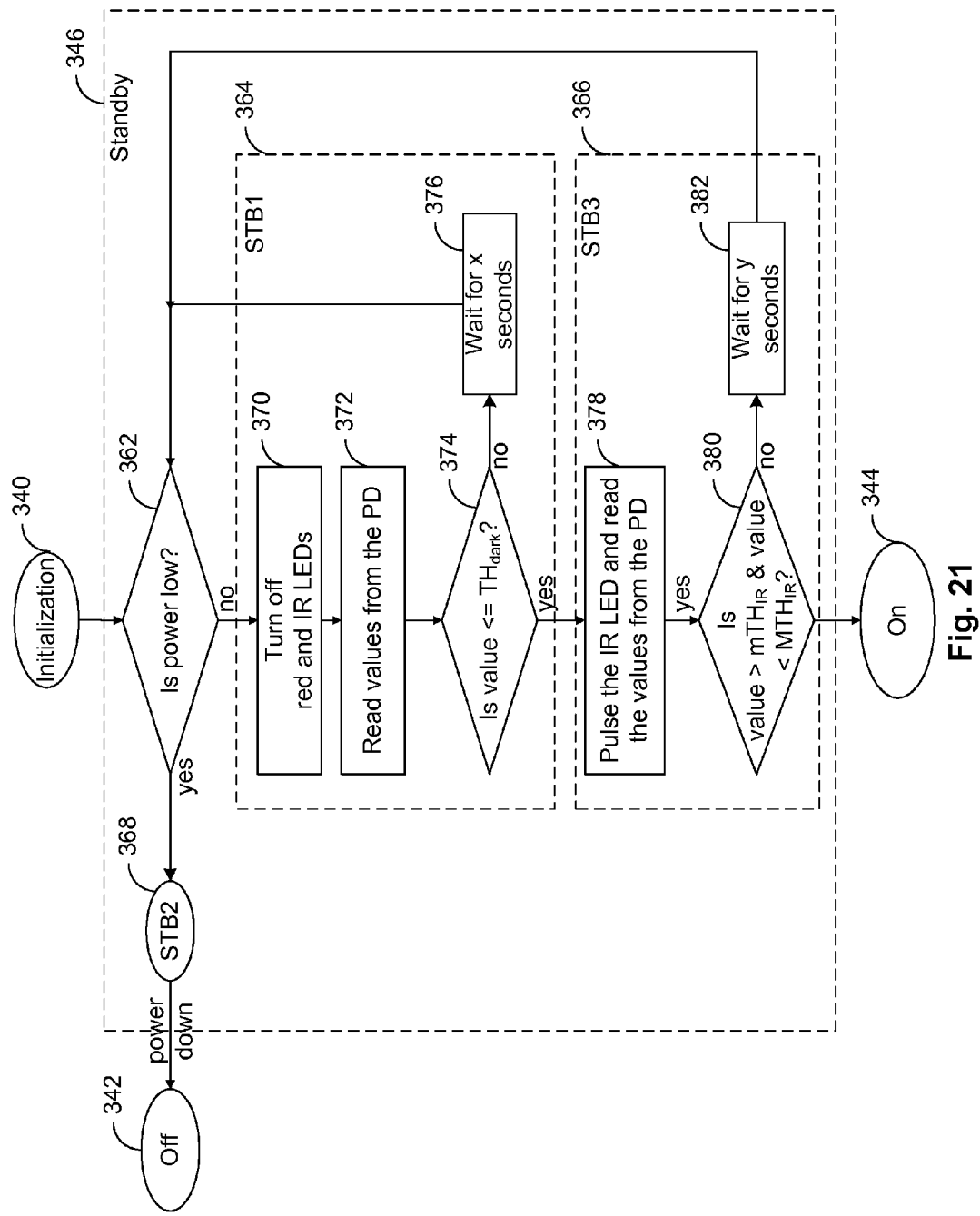
FIG. 21 illustrates a flowchart for transitioning between various standby states and other states of a pulse oximeter.

FIG. 21 illustrates a flowchart for transitioning between various standby states and other states of a pulse oximeter. Once a pulse oximeter completes an initialization step 340, the pulse oximeter determines whether the power is low 362. If the power is not low, then the state changes to a first standby state STB1 364. In the STB1 state 364, the LEDs are turned off 370 and the output of the PD is read 372. If the value of the light value is not less than or equal to a predefined dark value 374 (meaning the sensor may not be connected to the patient), the pulse oximeter waits 376 for x seconds, e.g., 2 seconds, and detects again by first checking if the power is low 362.

If the value of the light value is less than or equal to the predefined dark value 374, then a no light condition is detected and the sensor can go into the standby state STB3. In the STB3 state, the IR LED is turned on 378 and a reading of the PD output is measured. If the reading is within a predefined range 380, the patient's finger is assumed to be in the sensor; the predefined range can be obtained experimentally. The state of the sensor is then placed into the on state 344.

If the PD output is out of the predefined range 380, then the pulse oximeter waits 382 for y seconds and detects again by first determining whether the power is low 362. No matter what state the pulse oximeter is in, once a low power condition occurs the pulse oximeter goes to the standby state STB2 368. In the STB2 state 368, only the wireless communication and a few components are active. Most of the components are off, including the LEDs, the pulse oximeter front end, etc. The pulse oximeter repeatedly sends low power warnings to the bedside monitor to warn the patient and the patient care provider. From the standby state STB2 368, the oximeter can transition to the off state 342.

Figure 22A:
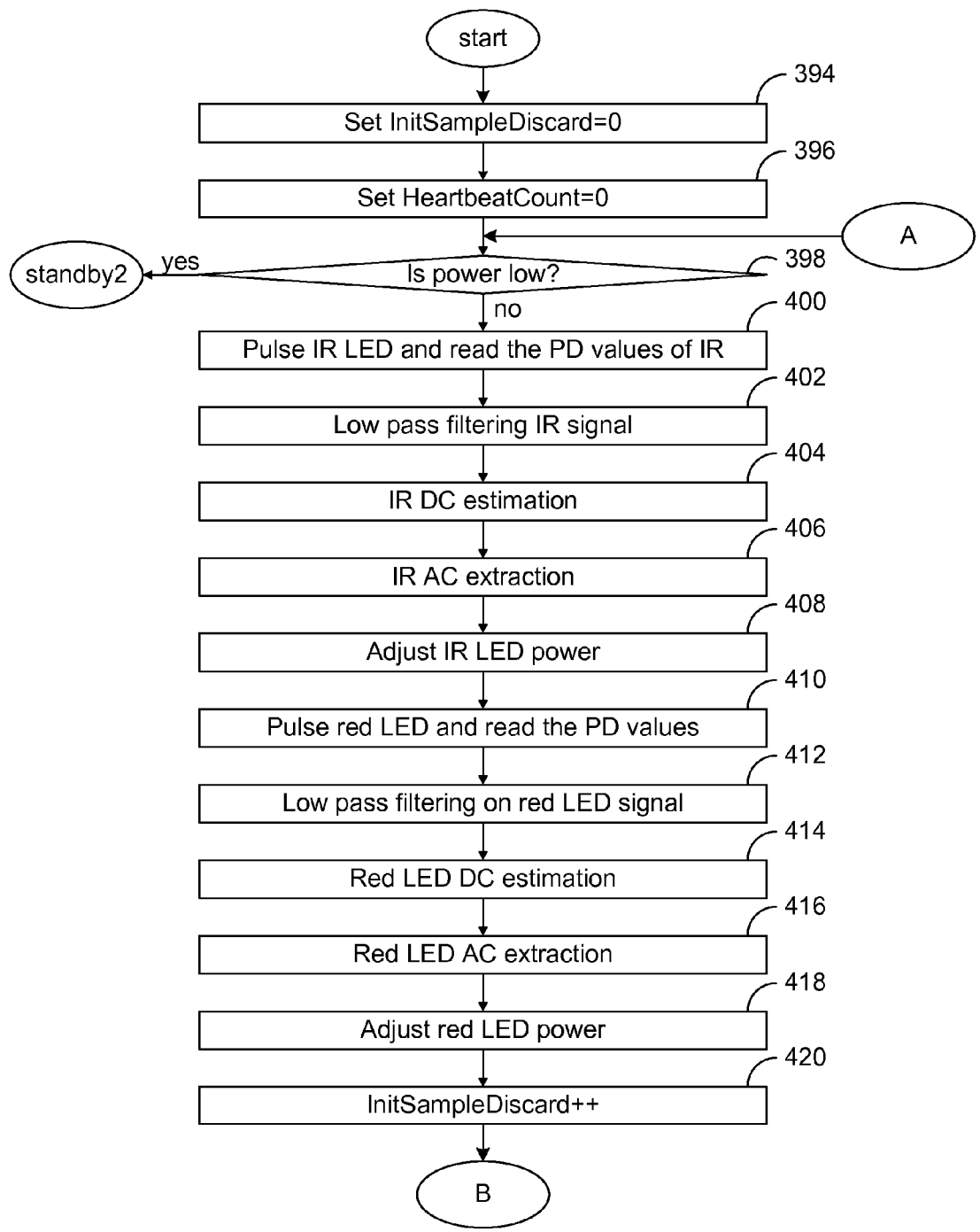
FIGS. 22a-22b illustrate a flowchart for operating a pulse oximeter during the ON state.
Figure 22B:
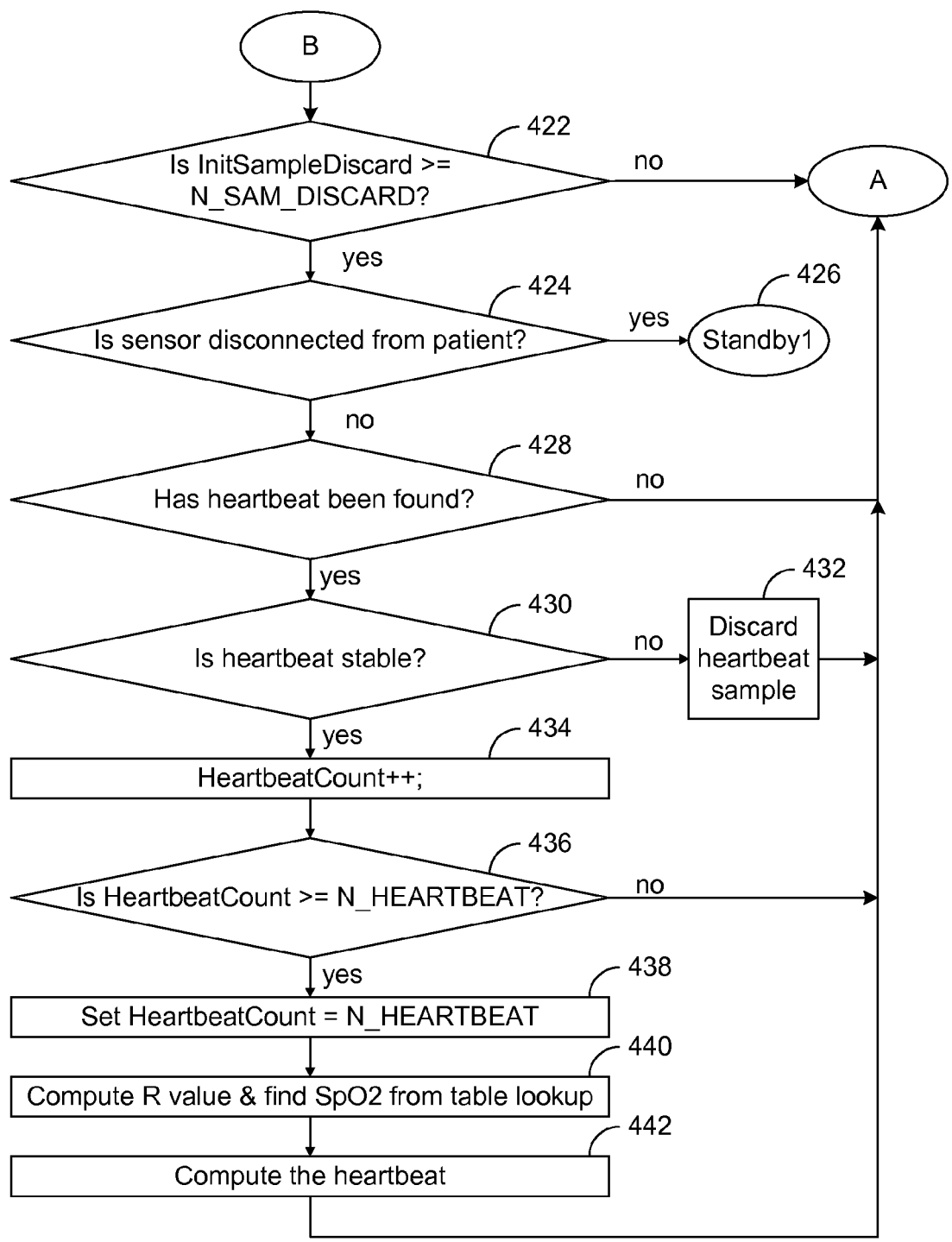

FIGS. 22a-22b illustrate a flowchart for operating an oximeter in an ON state of the pulse oximeter. When the pulse oximeter is first turned on, an "InitSampleDiscard" variable is set to zero 394 and a "HeartbeatCount" variable is also set to zero 396. Next, the pulse oximeter checks if the power is low 398. If it is, then the pulse oximeter goes into the STB2 state.

If the power is not low, the pulse oximeter pulses/turns on the IR LED and reads the PD output 400. The PD output values can be stored in a rolling based array of N elements, say IR0, . . . , IRN−1. A low pass filter is applied to the IR array (otherwise referred to as an IR signal) 402. The low pass filter can be a FIR hamming window low pass filter of order 51 and the cut off frequency of 10 Hz with attenuation 50 dB. Then, the DC tracking is used to get the DC component of the IR signal 404. The DC component can be removed from the IR signal to get the AC component of the IR signal 406. If the IR signal is out of a predefined target range, the IR LED power can be adjusted 408 for the next samples. For instance, if the IR signal is over the target range, it can mean the IR power is too high and needs to be lowered. On the other hand, if the IR data is below the target range, it can mean the IR power is too low and needs to be raised. The same process can be used for the red LED to get the AC component of the red LED data 410-416 and adjust the red LED's power if needed 418.

When the patient is ready to be sampled (e.g., the patient's finger is connected to the sensor holder), a predefined number of initial samples ("N_SAM_DISCARD"), e.g., 300 samples, is discarded since the data may not be stable when the sensor initially starts. The number of initial samples is counted by sequentially increasing the InitSampleDiscard variable 420. Next, the pulse oximeter determines whether the InitSampleDiscard variable is greater than or equal to the predefined number of initial samples to be discarded 422. If the InitSampleDiscard variable is not greater than or equal to the predefined number of initial samples to be discarded, then the pulse oximeter loops back to perform another sampling by first determining whether the power is low 398.

If the InitSampleDiscard variable is greater than or equal to the predefined number of initial samples to be discarded, the pulse oximeter detects whether or not the pulse oximeter is disconnected from the patient 424. Various methods can be used to determine whether the pulse oximeter is disconnected from the patient, including a patient detection algorithm as described below, whether values of the photodiode of the pulse oximeter are within a range of values as described in the STB1 state and the STB2 state as illustrated in FIG. 21, or by another method for determining whether an oximeter is properly connected to the patient.

If the pulse oximeter detects that the pulse oximeter is disconnected from the patient, then the pulse oximeter goes into the STB1 state 426. If not, the pulse oximeter determines whether a heartbeat for the patient is found 428. Various methods can be used to determine whether a heartbeat has been found, including a heartbeat tracking algorithm as described below.

If the heartbeat for the patient is not found, then the pulse oximeter loops back to perform another sampling by first determining whether the power is low 398. If the heartbeat of the patient is found, then the pulse oximeter determines if the heartbeat is stable 430. Various methods can be used to determine whether a heartbeat is stable, including the heartbeat tracking algorithm as described below.

If the heartbeat is not stable, then the heartbeat sample is discarded 432, and the pulse oximeter loops back to perform another sampling by first determining whether the power is low 398. If the heartbeat sample is stable, then the HeartbeatCount variable is sequentially increased 434. If the HeartbeatCount variable is not greater than or equal to a predefined number of heartbeats ("N_HEARTBEAT") 436, the pulse oximeter loops back to perform another sampling by first determining whether the power is low 398. If the HeartbeatCount variable is greater than or equal to the predefined number of heartbeats, then the predefined number of heartbeats is set to be equal to the HeartbeatCount variable 438.

Next, a ratio of the AC energy of red samples versus the AC energy of the IR samples in one heartbeat ("R") is computed, and the blood oxygen saturation is then obtained from a table lookup that maps the ratio R to the blood oxygen saturation by experimental data 440. The heartbeat rate can be calculated 442 using the N_HEARBEAT variable and the frequency of sampling. Once the heartbeat rate is computed, the pulse oximeter loops back to perform another sampling by first determining whether the power is low 398.

Heartbeat Tracking Algorithm

On the IR data samples, a heartbeat tracking algorithm is applied to track the heartbeat. The heartbeat algorithm tracks the minimum and maximum of the IR data and when the minimum and the maximum happen.

In the beginning, the algorithm first decides the direction of the heartbeat signal. The heartbeat signal can be plotted as IR sample values versus time. If a minimum value happens earlier than a maximum value for a predefined number of IR samples, say 20 samples, the heartbeat signal is in the uptrend. If the maximum value happens earlier by the predefined number of samples, the heartbeat signal is in the downtrend. Otherwise, the direction is not found yet. If the direction is not determined, more samples are collected until the direction is found.

When it is in the uptrend the algorithm searches for the local maximum value. During the uptrend, when a new IR sample is greater than the previous local maximum value, the new IR sample is set as the local maximum value and a maximum index is changed to be the sample time. Also, the local minimum value is reset to the IR sample and the minimum index is reset to the sample time too. The local minimum value and its index are not reset if no further local maximum is found. Then, the local minimum value is replaced if the new sample is less than the local minimum. The local maximum is obtained if the minimum index is greater than the local maximum index by the predefined value. If this happens the heartbeat signal is now in the downtrend. The local maximum can be stored in an array of maximum and minimum values for IR samples.

In the downtrend, repeat the similar operations as in the uptrend. That is, when a new IR sample is smaller in value than the stored minimum value, the new IR sample value replaces the stored minimum value and the new IR sample's index replaces the stored minimum index. Also, the maximum value is reset to the new minimum value and the maximum index is reset to the new minimum index. If a new minimum value is not found, the maximum value and its index are not reset and are replaced when a new IR sample is greater in value than the maximum value. The process continues until the maximum index is larger than the minimum index by the predefined value. Then, the local minimum is found and the heartbeat signal is now in the uptrend. The local minimum can be stored in an array of maximum and minimum values for IR samples.

A heartbeat is then defined from the maximum to the next maximum (or from the minimum to the next minimum) in the array of sampling times of the local maximum (or the local minimum values) for IR samples. In preferred embodiments, the array of maximum and minimum values for IR samples consists of eight entries and is rolling based, i.e., a new value replaces the oldest value in the array when the array is full. Thus, the array is a first-in first-out array. If the differences between the sampling times of any two successive local maximum values (or two successive local minimum values) of the array for the IR samples are all less than a predefined threshold value, the IR samples are deemed to be stable.

When the heartbeat is stable, the eight values in the array are averaged and the heartbeat rate ("HR") can be calculated by the following formula:

$$HR = 60 \cdot F/N\_ave, \qquad (2)$$

where F is the sampling frequency in Hz (samples per second), N_ave is the average number of samples per second.

In addition, when the heartbeat is stable, a ratio of the AC energy of red samples versus the AC energy of the IR samples in one heartbeat is computed. The blood oxygen saturation is then obtained from a table lookup that map the ratio to the blood oxygen saturation by experimental data. Since there can be eight heartbeats, the average of the eight blood oxygen saturation values is reported.

Patient Detection Algorithm

A patient detection algorithm is also developed to detect if the patient is connected to the pulse oximeter for sampling oximetry measurements. First, if the difference between the minimum value and the maximum value of a heartbeat signal is less than a predefined threshold, a counter ("heart_ac_MINMAX_LOW") is sequentially increased to track this case. If not, the counter is reset to zero. When the counter reaches a predefined number, say 10 heartbeats, it can mean that heartbeats are not detected (e.g., the patient's finger, toe, earlobe or other body part may not be in the sensor holder of the pulse oximeter). Another case is when the sensor cannot find the minimum or the maximum value for an extended number of samples, e.g., 1500 samples. This might imply that there is no heartbeat or that the patient's body part is not properly connected to the sensor holder of the pulse oximeter.

For the condition where heartbeats are not detected, the pulse oximeter might be disconnected from the patient, rather than the patient not having a heartbeat. Thus, to further distinguish between a no heartbeat condition and a sensor disconnected case, the heartbeat signal of the patient is checked. If the heartbeat signal is within a predefined range, this indicates that the patient does not have a heartbeat. If the heartbeat signal is not within the predefined range, this indicates that the pulse oximeter is disconnected from the patient.

While the present invention has been described with reference to certain preferred embodiments or methods, it is to be understood that the present invention is not limited to such specific embodiments or methods. Rather, it is the inventor's contention that the invention be understood and construed in its broadest meaning as reflected by the following claims. Thus, these claims are to be understood as incorporating not only the preferred methods described herein but all those other and further alterations and modifications as would be apparent to those of ordinary skilled in the art.

We claim:

1. A patient monitoring system for monitoring vital signs, comprises:
   one or more sensors, wherein the sensors measure vital signs;
   a monitor station;
   a memory device; and
   one or more portable monitoring devices,
   wherein monitored data based on the measured vital signs is wirelessly transmitted from the sensors to the monitor station,
   wherein the monitor station issues one or more alarms to certain ones of the portable monitoring devices as a function of the monitored data,
   wherein a portion of the monitored data that pertains to the alarms is wirelessly transmitted to the certain ones of the portable monitoring devices and displayed by the certain ones of the portable monitoring devices,
   wherein one of the sensors is a pulse oximeter,
   wherein the pulse oximeter comprises a vital sign data collector, a battery board, and a patch,
   wherein the vital sign data collector and the battery board are detachable from the patch,
   wherein the vital sign data collector comprises a red light emitting diode ("LED"), an infrared ("IR") LED, and a photodiode ("PD"),
   wherein the pulse oximeter has a first standby state, a second standby state, and a third standby state, wherein in the first standby state, the oximeter determines whether an object is under measurement by the oximeter, wherein in the third standby state, the oximeter determines whether light readings from the red LED and infrared LED are within an acceptable predefined range, wherein in the second standby state, the oximeter goes into a power saving mode, wherein IR data samples are collected by pulsing the infrared LED over a period of time and reading values from the PD to generate a heartbeat signal and wherein the pulse oximeter tracks local minimum values and local maximum values of the IR data samples, wherein the local minimum values and the local maximum values of the IR data samples and sampling times for the local minimum values and the local maximum values are stored in an array of eight entries, wherein the array is stored in the memory device, and wherein the array is a first-in first-out array, and wherein a next local maximum value and a next local minimum value are inputted into array.

2. The patient monitoring system of claim 1 wherein each of the alarms is assigned a priority and wherein the certain ones of the portable monitoring devices generate the alarms in order of the respective priority of the alarms.

3. The patient monitoring system of claim 1 further comprising one or more bedside monitors for displaying the monitored data, wherein the bedside monitors route the monitored data from the sensors to the monitor station.

4. The patient monitoring system of claim 3 wherein each of the sensors is paired with one of the bedside monitors.

5. The patient monitoring system of claim 3 wherein the portion of the monitored data that pertains to the alarms is wirelessly transmitted to certain ones of the bedside monitors and displayed by the certain ones of the bedside monitors.

6. The patient monitoring system of claim 3 wherein the bedside monitors measure environmental conditions and records audio/video ("AV") and wherein the monitored data includes the measured environmental conditions and the recorded AV.

7. The patient monitoring system of claim 3 wherein each of the bedside monitors comprise a processor, a display, data storage, an identification unit, a power source, one or more environmental sensors, a video camera, a microphone, an alarm unit, and a wireless interface.

8. The patient monitoring system of claim 3 wherein one or more of the sensors are associated with a patient, and said one or more of the sensors is associated with one of the beside monitors such that the measured vital signs from the said one or more of the sensors is wirelessly transmitted to said one of the beside monitors.

9. The patient monitoring system of claim 1 wherein each of the sensors comprise one or more vital sign data collectors, a processor, a wireless interface, data storage, an identification unit, and a battery unit.

10. The patient monitoring system of claim 1 wherein the patch comprises a light emitting diode ("LED") driver, a pulse oximeter system-on-chip ("SOC"), a wireless SOC, and an antenna chip.

11. The patient monitoring system of claim 1 wherein the pulse oximeter determines whether a heartbeat rate of a patient is stable by determining whether the difference between the sampling times of any two successive local maximum values of the entries in the array are all less than a predefined threshold value.

12. The patient monitoring system of claim 1 wherein the pulse oximeter determines whether a patient is connected to the pulse oximeter as a function of the local minimum values, of the local maximum values, and of the heartbeat signal.

13. The patient monitoring system of claim 1 wherein the monitor station comprises a processor, a display, an alarm unit, data storage, power supply, ID reader, ID writer, a microphone and a wireless interface.

14. The patient monitoring system of claim 13 wherein a patient is registered at the monitor station by creating a patient identification ("PID") for a patient and wherein a unique identification number for each of said certain ones of the sensors is read by the ID reader and the unique identification number is associated with the PID in a computer database.

15. The patient monitoring system of claim 1 wherein each of the portable monitoring devices comprises a processor, a display, an alarm unit, a battery board, a microphone, and a wireless interface.

16. The patient monitoring system of claim 1 wherein one or more access points are used to route wireless transmission from the sensors to the monitor station.

* * * * *